(12) United States Patent
Deshpande et al.

(10) Patent No.: US 7,375,213 B2
(45) Date of Patent: May 20, 2008

(54) METHODS OF PRODUCING C-ARYL GLUCOSIDE SGLT2 INHIBITORS

(75) Inventors: Prashant P. Deshpande, Princeton, NJ (US); Bruce A. Ellsworth, Princeton, NJ (US); Janak Singh, Lawrenceville, NJ (US); Theodor W. Denzel, Regensburg (DE); Chiajen Lai, Kendall Park, NJ (US); Gerard Crispino, Lawrenceville, NJ (US); Michael E. Randazzo, East Windsor, NJ (US); Jack Z. Gougoutas, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 565 days.

(21) Appl. No.: 10/745,075

(22) Filed: Dec. 23, 2003

(65) Prior Publication Data

US 2004/0138439 A1    Jul. 15, 2004

Related U.S. Application Data

(60) Provisional application No. 60/437,847, filed on Jan. 3, 2003.

(51) Int. Cl.
*C07H 15/203* (2006.01)
*C07H 15/20* (2006.01)
*C07H 1/00* (2006.01)

(52) U.S. Cl. .................. 536/124; 536/1.11; 536/17.2; 536/17.3; 536/17.4; 536/17.5; 536/18.4

(58) Field of Classification Search ............... 536/124, 536/1.11, 17.2, 17.3, 17.4, 17.5, 18.4
See application file for complete search history.

(56) References Cited

U.S. PATENT DOCUMENTS 6,414,126 B1   7/2002   Ellsworth et al.

6,515,117 B2   2/2003   Ellsworth et al.
6,774,112 B2   8/2004   Gougoutas

FOREIGN PATENT DOCUMENTS

| EP | 0997472 | 5/2000 |
|---|---|---|
| WO | WO 01/27128 | 4/2001 |
| WO | 02083066 | 10/2002 |

OTHER PUBLICATIONS

Greene, T.W. et al., Protective Groups in Organic Synthesis, Third Edition, John Wiley & Sons, Inc., publ. (1999) (table of contents).
Johannsson, G. et al., "Growth Hormone Treatment of Abdominally Obese Men Reduces Abdominal Fat Mass, Improves Glucose and Lipoprotein Metabolism, and Reduces Diastolic Blood Pressure", Journal of Clinical Endocrinology and Metabolism, vol. 82, No. 3, pp. 727-734 (1997).
Kuribayashi et. al., Tetrahedron Letters, 39, pp. 4537-4540 (1998).
Kuribayashi, et al., Journal of Carbohydrate Chemistry, 18(4), pp. 393-401 (1999).
Anthony G. M. Barrett et al., Total Synthesis of the Antifungal Agent Papulacandin D, J. Chem. Soc., Chem. Commun., 1995, pp. 1147-1148.
Anthony G. M. Barrett et al., Total Synthesis and Structural Elucidation of the Antifungal Agent Papulacandin D, J. Org. Chem., 1996, pp. 1082-1100, vol. 61.
Vincente Lecomte et al., Improved Addition of Phenyllithium to Hindered Ketones by the the use of Non-polar Media, Tetrahedron Letters, 2002 pp. 3463-3465, vol. 43.
Vincente Lecomte et al., Improved Addition of Organolithium Reagents to Hindered and/or Enolisable Ketones, Tetrahedron, 2003, pp. 2169-2176, vol. 59.

*Primary Examiner*—Shaojia Anna Jiang
*Assistant Examiner*—Everett White
(74) *Attorney, Agent, or Firm*—McDonnell Boehnen Hulbert & Berghoff LLP

(57) ABSTRACT

Method for the production of C-aryl glucoside SGLT2 inhibitors useful for the treatment of diabetes and related diseases. and intermediates thereof. The C-aryl glucosides may be complexed with amino acid complex forming reagents.

21 Claims, No Drawings

METHODS OF PRODUCING C-ARYL GLUCOSIDE SGLT2 INHIBITORS

This application claims priority from U.S. Provisional Application 60/437,847 filed Jan. 3, 2003 which is incorporated herein by reference.

FIELD OF INDUSTRIAL APPLICABILITY OF THE INVENTION

The present invention is directed to C-aryl glucoside compounds, which are inhibitors of sodium dependent glucose transporters found in the intestine and kidney (SGLT2), and more particularly to a process of producing such compounds, for example 1-C-(substituted diphenylmethane-3-yl)-β-D-glucopyranose, through unique processes for producing useful intermediates thereof in a manner which enables the final products to be produced in a one-pot process with fewer intermediate compounds having to be isolated. The invention is also directed to crystalline complexes of the C-aryl glucoside compounds formed with an amino acid complex forming agent.

BACKGROUND OF THE INVENTION

Approximately 100 million people worldwide suffer from type II diabetes [non-insulin dependent diabetes mellitus (NIDDM)], which is characterized by hyperglycemia due to excessive hepatic glucose production and peripheral insulin resistance, the root causes of which are as yet not clearly understood. Hyperglycemia is considered to be the major risk factor for the development of diabetic complications, and is likely to contribute directly to the impairment of insulin secretion seen in advanced NIDDM. Normalization of plasma glucose in NIDDM patients would be predicted to improve insulin action, and to offset the development of diabetic complications. An inhibitor of the sodium-dependent glucose transporter (SGLT2) in the kidney would be expected to aid in the normalization of plasma glucose levels, and perhaps body weight, by enhancing glucose excretion.

Hyperglycemia is a hallmark of type II diabetes; consistent control of plasma glucose levels in diabetes can offset the development of diabetic complications and beta cell failure seen in advanced disease. Plasma glucose is normally filtered in the kidney in the glomerulus and actively reabsorbed in the proximal tubule. SGLT2 appears to be the major transporter responsible for the reuptake of glucose at this site. The SGLT specific inhibitor phlorizin or closely related analogs inhibit this reuptake process in diabetic rodents and dogs resulting in normalization of plasma glucose levels by promoting glucose excretion without hypoglycemic side effects. Long term (6 month) treatment of Zucker diabetic rats with an SGLT2 inhibitor has been reported to improve insulin response to glycemia, improve insulin sensitivity, and delay the onset of nephropathy and neuropathy in these animals, with no detectable pathology in the kidney and no electrolyte imbalance in plasma. Selective inhibition of SGLT2 in diabetic patients would be expected to normalize plasma glucose by enhancing the excretion of glucose in the urine, thereby improving insulin sensitivity, and delaying the development of diabetic complications.

Ninety percent of glucose reuptake in the kidney occurs in the epithelial cells of the early S1 segment of the renal cortical proximal tubule, and SGLT2 is likely to be the major transporter responsible for this reuptake. SGLT2 is a 672 amino acid protein containing 14 membrane-spanning segments that is predominantly expressed in the early S1 segment of the renal proximal tubules. The substrate specificity, sodium dependence and localization of SGLT2 are consistent with the properties of the high capacity, low affinity, sodium dependent glucose transporter previously characterized in human cortical kidney proximal tubules. In addition, hybrid depletion studies implicate SGLT2 as the predominant Na$^+$/glucose cotransporter in the S1 segment of the proximal tubule, since virtually all Na-dependent glucose transport activity encoded in mRNA from rat kidney cortex is inhibited by an antisense oligonucleotide specific to rat SGLT2.

SGLT2 is a candidate gene for some forms of familial glucosuria, a genetic abnormality in which renal glucose reabsorption is impaired to varying degrees. None of these syndromes investigated to date map to the SGLT2 locus on chromosome 16. However, studies involving highly homologous rodent SGLTs strongly implicate SGLT2 as the major renal sodium-dependent transporter of glucose and suggest that the glucosuria locus that has been mapped encodes an SGLT2 regulator. Inhibition of SGLT2 would be predicted to reduce plasma glucose levels via enhanced glucose excretion in diabetic patients.

C-aryl glucosides, a class of SGLT2 inhibitors, have been observed to act as orally active antidiabetic agents. In particular, these C-aryl glucoside SGLT2 inhibitors have been found to be useful for treating or delaying the progression or onset of diabetes, especially type I and type II diabetes, including complications of diabetes such as retinopathy, neuropathy, nephropathy and delayed wound healing, and related diseases such as insulin resistance and impaired glucose homeostasis (IGH), hyperglycemia, hyperinsulinemia, elevated blood levels of fatty acids or glycerol, obesity, hyperlipidemia including hypertriglyceridemia, Syndrome X, hypertension, atherosclerosis and related diseases, and for increasing high density lipid levels. The conditions, diseases, and maladies collectively referred to as "Syndrome X" (also known as Metabolic Syndrome) are detailed in Johannsson, J. Clin. Endrocrinol. Metab., 82, 727–34 (1997).

Such C-aryl glucoside SGLT2 inhibitors may be used alone or to complement existing therapy treatments, including sulfonylureas, thiazolidinediones, metformin, and insulin, and to avoid the potential side effects typically associated with the use of these other agents. Further details about the C-aryl glucosides and derivatives thereof, may be found in PCT World Application WO 01/27128-A1, U.S. Pat. No. 6,414,126, U.S. patent application Ser. No. 10/151,436, and U.S. patent application Ser. No. 10/117,914, the entire disclosures of which are incorporated herein by reference.

A method of producing C-aryl glucoside SGLT2 inhibitors which provides a telescoped or one-pot operation, or optionally a multi-vessel reaction, and which minimizes the production of intermediates during production of the final product for improved yield and purity would be desirable. It would further be useful for such a method to be stereoselective in operation, to allow for the production of a substantially enantiomerically pure product. Such a method could be applied to the preparation of compounds including but not limited to 1-C-(4'-ethyldiphenylmethane-3-yl)-β-D-glucopyranose, 1-C-(6-methyl-4'-(methylthio)diphenylmethane-3-yl)-β-D-glucopyranose, 1-C-(6-chloro-4'-ethoxydiphenylmethane-3-yl)-β-D-glucopyranose. Also desirable is a method of forming crystalline complexes of the compounds synthesized.

SUMMARY OF THE INVENTION

The present invention is directed to a novel stereoselective process of producing C-aryl glucosides that can, in one option, be conducted in a one-pot operation with fewer steps than the alternative processes that involve one or more isolation of intermediate reaction products. The invention further comprises certain intermediates formed during these processes. In another embodiment the invention additionally comprises the preparation of crystalline complexes of the C-aryl glucosides In one aspect of the present invention, there is provided a process for preparing compounds of Formula (I) and pharmaceutically acceptable complexes thereof

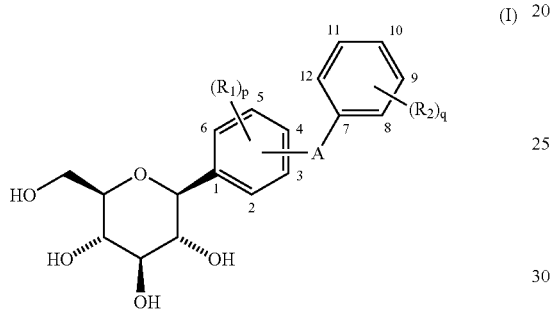
(I)

wherein:
  $R_1$ is selected from the group consisting of hydrogen, a hydroxy group, bromine, chlorine, fluorine, an alkyl group, an alkoxy group, an alkylthio group, and an arylthio group, where p is 1 to 4, and with the proviso that bromine, chlorine and fluorine, when present, are only present in at least one of the 3-, 4- and 5-positions;
  $R_2$ is selected from the group consisting of hydrogen, a hydroxy group, chlorine, fluorine, an alkyl group, an alkoxy group, and an alkylthio group, where q is 1 to 5; and
  A is selected from the group consisting of a covalent bond, O, S, NH, and $(CH_2)_n$ where n is 1 to 3, and with the provisos that
    when A is in the 4-position, $R_1$ is not bromine;
    when one of $R_1$ is bromine; and if A is in the 3- or 6-position, then bromine is in the 5-position,
    if A is in the 2- or 5-position, then bromine is in the 3-position, and
    when bromine is in the 3-position, and A is in the 2- or 5-position, then $R_1$ groups in the 4- and 6-positions are the same and are not bromine, chlorine or fluorine, and
    when bromine is in the 5-position, and A is in the 3- or 6-position, then $R_1$ groups in the 2- and 4-positions are the same and are not bromine, chlorine or fluorine; said method comprising
a) forming a compound of Formula (IV) from a lactone protected with an acid-labile protecting group

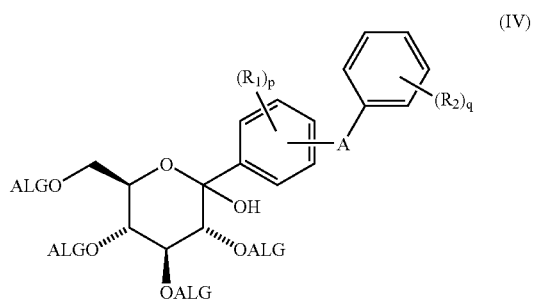
(IV)

b) glycosidation of the compound of Formula (IV) with simultaneous removal of the acid-labile protecting group to form a compound of Formula (V);

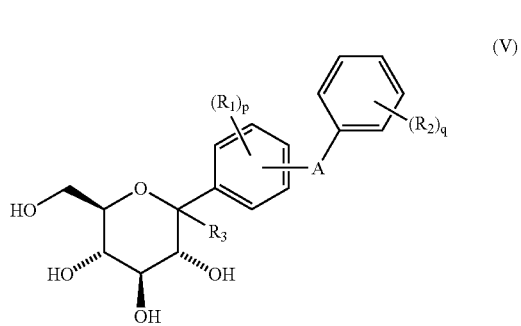
(V)

c) reacting the compound of Formula (V) with an acylating agent to form a compound of Formula (VI);

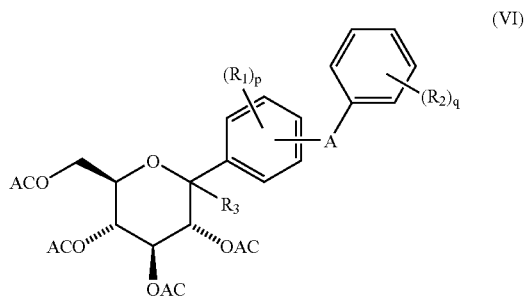
(VI)

d) reducing the compound of Formula (VI) to provide a compound of Formula (VII); and

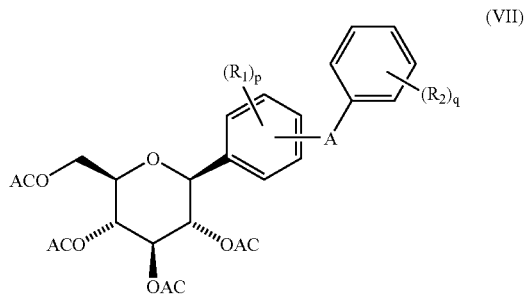
(VII)

e) removing acyl protecting group from the compound of Formula (VII) to provide a compound of Formula (I);

wherein $R_1$, $R_2$, A, p and q are as defined hereinabove, and AC is an acyl protecting group.

In a further embodiment the invention comprises a method of forming C-aryl glucoside compounds comprising reacting a compound of Formula (VI)

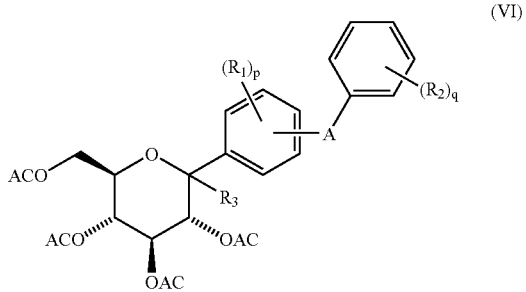

(VI)

with a reducing reagent; wherein $R_1$ is selected from the group consisting of hydrogen, a hydroxy group, bromine, chlorine, fluorine, an alkyl group, an alkoxy group, an alkylthio group, and an arylthio group, where p is an integer from 1 to 4, and with the proviso that bromine, chlorine and fluorine, when present, are only present in at least one of the 3-, 4- and 5-positions;

$R_2$ is selected from the group consisting of hydrogen, a hydroxy group, chlorine, fluorine, an alkyl group, an alkoxy group, and an alkylthio group, where q is an integer from 1 to 5; and A is selected from the group consisting of a covalent bond, O, S, NH, and $(CH_2)_n$ where n is an integer from 1 to 3, and with the proviso that when A is in the 4-position, $R_1$ is not bromine;

with the proviso that when one of $R_1$ is bromine; and if A is in the 3- or 6-position, then bromine is in the 5-position, if A is in the 2- or 5-position, then bromine is in the 3-position, and when bromine is in the 3-position, and A is in the 2- or 5-position, then $R_1$ groups in the 4- and 6-positions are the same and are not bromine, chlorine or fluorine, and when bromine is in the 5-position, and A is in the 3- or 6-position, then $R_1$ groups in the 2- and 4-positions are the same and are not bromine, chlorine or fluorine;

$R_3$ is selected from the group consisting of an alkoxy group, an alkenyloxy group, an alkylthio group and an alkenylthio group; and AC is an acyl protecting group;

to form a compound of Formula (VII)

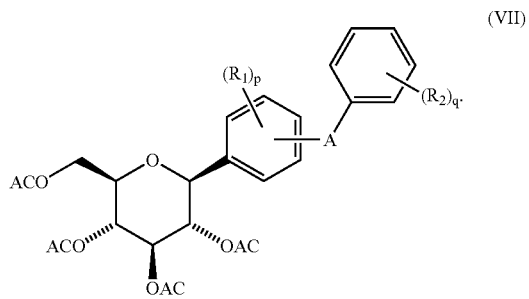

(VII)

In a preferred embodiment of the present invention, there is provided a process for preparing compounds of Formula (IA) and pharmaceutically acceptable complexes thereof.

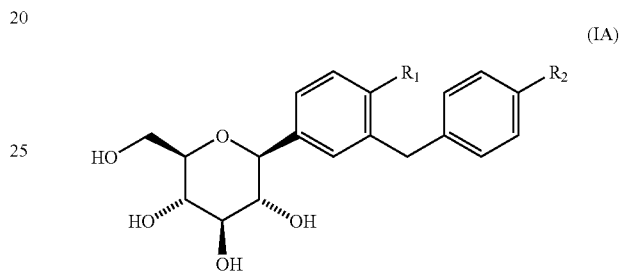

(IA)

wherein:

$R_1$ is selected from the group consisting of hydrogen, an alkyl group, and chlorine; and $R_2$ is selected from the group consisting of hydrogen, an alkyl group, an alkoxy group, and an alkylthio group.

In another aspect of the present invention, there are provided novel intermediate compounds and methods of preparing the same, which are useful in the preparation of the compounds of Formula (I). The novel intermediate compounds of the present invention include:

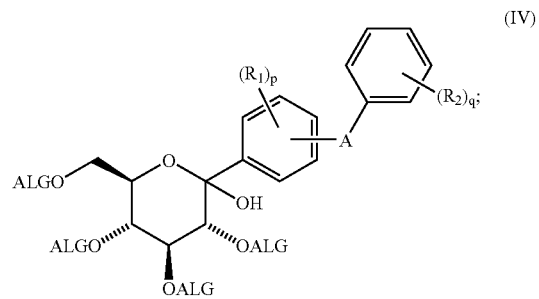

(IV)

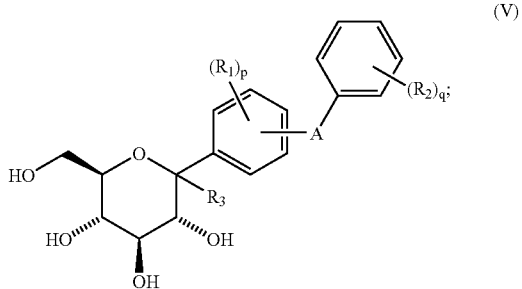

(V)

-continued

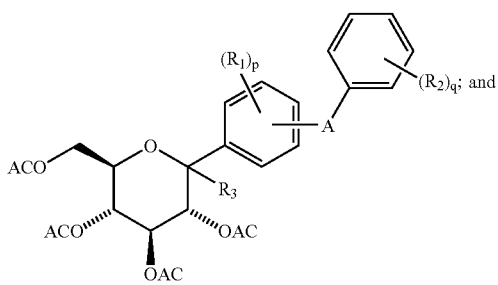
(VI)

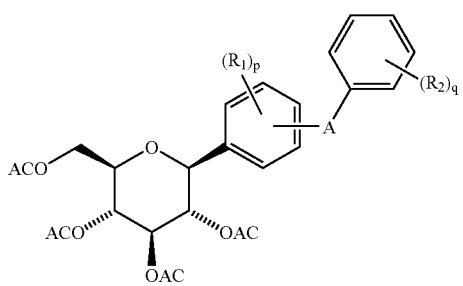
(VII)

wherein:

$R_1$, $R_2$, A, p and q are as defined above;

$R_3$ is selected from the group consisting of an alkoxy group, an alkenyloxy group, an alkylthio group and an alkenylthio group;

AC is an acyl protecting group such as $CH_3CO$—; and

ALG is an acid labile protecting group.

DETAILED DESCRIPTION OF THE INVENTION

The present invention is directed to a process of producing C-aryl glucosides and crystalline complexes thereof, to processes for producing intermediate compounds and to novel intermediate compounds. The process of the present invention can be conducted in a multi-vessel reaction involving one or more isolations of intermediates, or optionally in a telescoped reaction that entails fewer steps than the multi-vessel reaction or other conventional processes for producing such compounds. Certain processes of the present invention therefore can produce C-aryl glucosides, complexes and intermediates thereof at reduced costs and labor, while delivering enhanced purity and yield.

It has now been discovered that using acid labile protecting groups, especially the cost effective silyl-containing acid labile protecting groups, and acyl protecting groups at corresponding steps of the present process to protect hydroxy groups, significantly enhances the yield, stereoselectivity, and economy of the synthesis of the present compounds. During the process of the present invention, deprotection of the hydroxy groups can be accomplished under acidic or basic conditions depending on the nature of the protecting group by standard methods known in the art. A summary of the procedures suitable for deprotecting the hydroxy group is described in Greene, T. W. and Wuts, P. G. M., Protecting Groups in Organic Synthesis, 3$^{rd}$ edition, John Wiley & Son, Inc. (1999), which is incorporated herein by reference.

Listed below are definitions of various terms used in the description of the present invention. These definitions apply to the terms as they are used throughout the specification (unless they are otherwise limited in specific instances) either individually or as part of a larger group.

The following abbreviations are employed herein:
Ph=phenyl
t-Bu=tertiary butyl
Me=methyl
Et=ethyl
TMS=trimethylsilyl
THF=tetrahydrofuran
Tol=toluene
$BF_3.Et_2O$=borotrifluoride-etherate
$CH_3CN$=acetonitrile
EtOAc=ethyl acetate
MeOH=methanol
MSOH=methane sulfonic acid
EtOH=ethanol
$Et_3SiH$=triethylsilyl hydride
i-PrOH=isopropanol
$Ac_2O$=acetic anhydride
AcOH=acetic acid
$Et_3N$=triethylamine
DIPEA=i-$Pr_2NEt$=N,N'-diisopropylethylamine
DMAP=4-dimethylaminopyridine
n-BuLi=n-butyllithium
NaOH=sodium hydroxide
TLC=thin layer chromatography
HPLC=high performance liquid chromatography
GC=gas chromatography
AP=area percent ratio
KF=Karl Fisher
LOD=loss on drying As used herein, the term "glucoside" may be used equivalently and interchangeably with the terms "glycoside," "glucopyranose" or "glucopyranoside," meaning an acetal molecule derived from a combination of hydroxy compounds with glucose as a sugar constituent.

Unless otherwise indicated, the term "lower alkyl" as employed herein alone or as part of another group includes straight and branched chain hydrocarbons containing 1 to 8 carbons, and the terms "alkyl" and "alk" as employed herein alone or as part of another group includes straight and branched chain hydrocarbons containing 1 to 20 carbons preferably 1 to 10, more preferably 1 to 8, in the normal chain, such as methyl, ethyl, propyl isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like, as well as such groups including 1 to 4 substituents such as halo, for example F, Br, Cl, or I or $CF_3$, alkyl, alkoxy, aryl, aryloxy, aryl(aryl) or diaryl, arylalkyl, arylalkoxy, alkenyl, alkynyl, cycloalkyl, cycloalkenyl, cycloalkylalkyl, cycloalkylalkyloxy, optionally substituted amino, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially saturated (containing 1 or 2 double bonds) cyclic hydrocarbon groups containing 1 to 3 rings, including monocyclicalkyl, bicyclicalkyl, and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl, cyclododecyl, cyclohexenyl and the like, any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio and/or any of the alkyl substituents.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "alkanoyl" as used herein alone or as part of another group refers to alkyl linked to a carbonyl group.

Unless otherwise indicated, the term "lower alkenyl" as used herein by itself or as part of another group refers to straight or branched chain radicals of 2 to 8 carbons, and the term "alkenyl" as used herein by itself or as part of another group refers to straight or branched chained radicals of 2 to 20 carbons, preferably 2 to 12 carbons, and more preferably 2 to 8 carbons in the normal chain, which include one to six double bonds, in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "lower alkynyl" as used herein by itself or as part of another group refers to straight or branched chain radicals of 2 to 8 carbons, and the term "alkynyl" as used herein by itself or as part of another group refers to straight or branched chain radicals of 2 to 30 carbons, preferably 2 to 12 carbons, and more preferably 2 to 8 carbons in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

The terms "arylalkyl," "arylalkenyl," and "arylalkynyl" as used alone or as part of another group refer to alkyl, alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl."

Where alkenyl groups as defined above and alkynyl groups as defined above, respectively, have single bonds for attachment at two different carbons atoms, they are termed "alkenylene groups" and "alkynylene groups," respectively, and may optionally be substituted as defined above for "alkenyl" and "alkynyl."

Suitable alkylene, alkenylene or alkynylene groups $(CH_2)_s$ or $(CH_2)_r$ (where r is 1 to 8, preferably 1 to 5, and s is 1 to 5, preferably 1 to 3, which includes alkylene, alkenylene or alkynylene groups) as defined herein, may optionally include 1, 2, or 3 substituents which include alkyl, alkenyl, halogen, cyano, hydroxy, alkoxy, amino, thioalkyl, keto, $C_3$–$C_6$ cycloalkyl, alkylcarbonylamino, or alkylcarbonyloxy.

The term "halogen" or "halo" as used herein alone or as part of another group refers to chlorine, bromine, fluorine and iodine.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example, and may be optionally substituted through available carbon atoms with 1, 2, or 3 groups selected from hydrogen, halo, haloalkyl, alkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

Unless otherwise indicated, the term "lower alkoxy," "alkoxy," "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, and thioalkyl. These substituents may be further substituted with a carboxylic acid and/or any of the alkyl substituents as set out above.

Unless otherwise indicated, the term "lower alkylthio," "alkylthio," "arylthio" or "aralkylthio" as employed herein alone or as part of another group includes any of the above alkyl, aralkyl or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl or arylalkyl groups linked to a nitrogen atom.

Unless otherwise indicated, the term "acyl" as employed herein by itself or as part of another group, as defined herein, refers to an organic radical linked to a carbonyl (C=O) group; examples of acyl groups include any of the alkyl substituents attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6-, or 7-membered saturated or partially saturated ring which includes 1 to 2 hetero atoms such as nitrogen, oxygen and/or sulfur, linked through a carbon atom or a heteroatom, where possible, optionally via the linker $(CH_2)_r$ (where r is 1, 2, or 3). The above groups may include 1 to 4 substituents such as alkyl, halo, oxo, and/or any of the alkyl substituents set out herein. In addition, any of the cycloheteroalkyl rings can be fused to a cycloalkyl, aryl, heteroaryl, or cycloheteroalkyl ring.

Unless otherwise indicated, the term "heteroaryl" as used herein alone or as part of another group refers to a 5- or 6-membered aromatic ring, which includes 1, 2, 3 or 4 hetero atoms such as nitrogen, oxygen or sulfur, and such rings fused to an aryl, cycloalkyl, heteroaryl, or cycloheteroalkyl ring (e.g., benzothiophenyl or indolyl), and includes possible N-oxides. The heteroaryl groups may optionally include 1 to 4 substituents such as any of the alkyl substituents set out above.

The term "cycloheteroalkylalkyl" as used herein alone or as part of another group refers to cycloheteroalkyl groups as defined above linked through a C atom or heteroatom to a $(CH_2)_r$ chain.

The term "heteroarylalkyl" or "heteroarylalkenyl" as used herein alone or as part of another group refers to a heteroaryl group as defined above linked through a C atom or heteroatom to a —$(CH_2)_r$— chain, alkylene or alkenylene as defined above.

The term "five, six, or seven membered carbocycle or heterocycle" as employed herein refers to cycloalkyl or cycloalkenyl groups as defined above or heteroaryl groups or cycloheteroaryl groups as defined above, such as thiadiazole, tetrazole, imidazole or oxazole.

The term "polyhaloalkyl" as used herein refers to an "alkyl" group as defined above which includes from 2 to 9, preferably from 2 to 5, halogen substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halogen substituents, such as F or Cl, preferably F, such as $CF_3CH_2O$, $CF_3O$ or $CF_3CF_2CH_2O$.

In a particular aspect, the present invention relates to a novel process for preparing compounds of Formula (I),

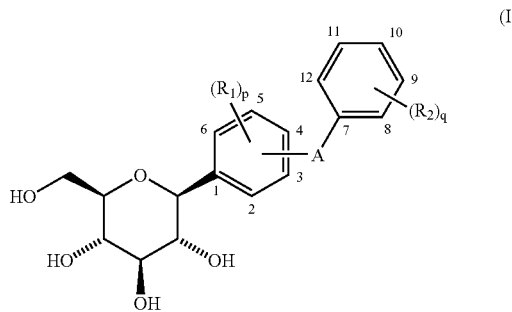

(I)

wherein:

$R_1$ is selected from the group consisting of hydrogen, a hydroxy group, bromine, chlorine, fluorine, an alkyl group, an alkoxy group, an alkylthio group, and an arylthio group, where p is 1 to 4, preferably 1 to 2, and most preferably 1, and with the proviso that bromine, chlorine and fluorine, when present, are only present in at least one of the 3-, 4- and 5-positions;

$R_2$ is selected from the group consisting of hydrogen, a hydroxy group, chlorine, fluorine, an alkyl group, an alkoxy group, and an alkylthio group, where q is 1 to 5, preferably 1 to 2, and most preferably 1; and A is selected from the group consisting of a covalent bond, O, S, NH, and $(CH_2)_n$ where n is 1 to 3, and with the proviso that when A is in the 4-position, $R_1$ is not bromine; with the proviso that when one of $R_1$ is bromine; and if A is in the 3- or 6-position, then bromine is in the 5-position, if A is in the 2- or 5-position, then bromine is in the 3-position, and when bromine is in the 3-position, and A is in the 2- or 5-position, then $R_1$ groups in the 4- and 6-positions are the same and are not bromine, chlorine or fluorine, and when bromine is in the 5-position, and A is in the 3- or 6-position, then $R_1$ groups in the 2- and 4-positions are the same and are not bromine, chlorine or fluorine.

In a preferred embodiment, the novel process of the present invention is well suited for preparing preferred compounds encompassed by Formula (IA)

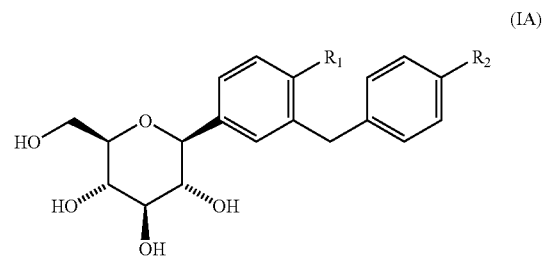

(IA)

wherein:

$R_1$ is selected from hydrogen, an alkyl group, chlorine; and $R_2$ is selected from hydrogen, an alkyl group, an alkoxy group, and an alkylthio group; and a pharmaceutically acceptable complex thereof.

In a particularly preferred embodiment, the novel process of the present invention is especially well suited for preparing preferred compounds of Formula (IA) and pharmaceutically acceptable complexes thereof above, wherein:

1) $R_1$ is hydrogen and $R_2$ is ethyl;
2) $R_1$ is chlorine and $R_2$ is ethoxy; and
3) $R_1$ is methyl and $R_2$ is methylthio.

The compounds of Formula (I) possess activity as inhibitors of sodium dependent glucose transporters found in the intestine and kidney of warm-blooded animals including humans and are useful therefore in the treatment of diabetes and the micro- and macrovascular complications of diabetes such as retinopathy, neuropathy, nephropathy and wound healing. In addition, the compounds of Formula (I) have been observed to be especially useful for treating or delaying the progression or onset of diabetes, especially type I and type II diabetes, including complications of diabetes such as retinopathy, neuropathy, nephropathy and delayed wound healing, and related diseases such as insulin resistance and impaired glucose homeostasis (IGH), hyperglycemia, hyperinsulinemia, elevated blood levels of fatty acids or glycerol, obesity, hyperlipidemia including hypertriglyceridemia, Syndrome X, hypertension, atherosclerosis and related diseases, and for increasing high density lipid levels. The conditions, diseases, and maladies collectively referred to as "Syndrome X" (also known as Metabolic Syndrome) are detailed in Johannsson, J. Clin. Endrocrinol. Metab., 82, 727–34 (1997) incorporated herein by reference.

The present invention also relates to novel intermediate compounds, which are useful in the preparation of the compounds of Formula (I). The novel intermediate compounds of the present invention include:

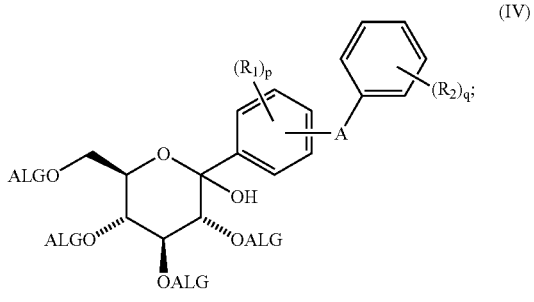

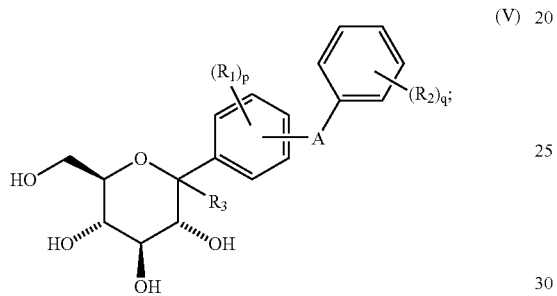

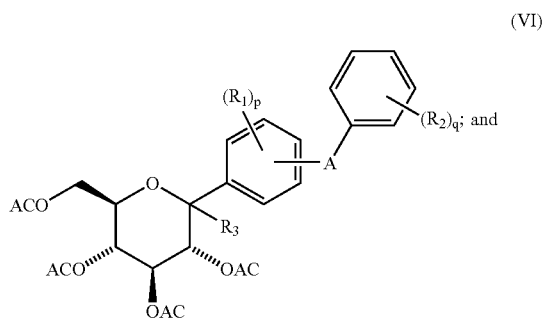

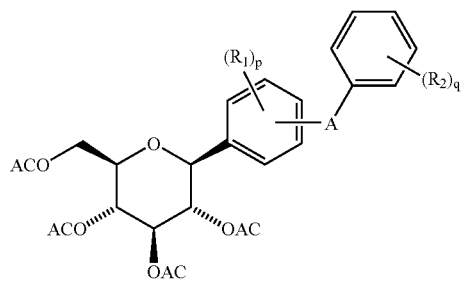

wherein:
$R_1$, $R_2$, A, p and q are as defined for compounds of Formula (I) above;
$R_3$ is selected from an alkoxy group, an alkenyloxy group, an alkylthio group and an alkenylthio group;
AC is an acyl protecting group such as $CH_3CO$—; and
ALG is an acid labile protecting group.

The acid labile protecting group, useful for protecting hydroxy groups, is preferably selected from methoxymethyl ether, methylthiomethyl ether, 2-methoxyethoxymethyl ether, bis(2-chloroethoxy)methyl ether, tetrahydropyranyl ether, tetrahydrothiopyranyl ether, 4-methoxytetrahydropyranyl ether, 4-methoxytetrahydrothiopyranyl ether, tetrahydrofuranyl ether, tetrahydrothiofuranyl ether, 1-ethoxyethyl ether, 1-methyl-1-methoxyethyl ether, 2-(phenylselenyl) ethyl ether, t-butyl ether, allyl ether, triphenylmethyl ether, α-naphthyldiphenylmethyl ether, p-methoxyphenyldiphenyl methyl ether, trialkylsilyl ether such as trimethylsilyl ether and triethylsilyl ether, isopropyldimethylsilyl ether, t-butyldimethylsilyl ether and t-butyldiphenylsilyl ether, for example.

In one particular aspect of the present invention, the process of preparing the compound of Formula (I) is generally conducted by reacting glucono-1,5-lactone having hydroxy groups protected by acid labile protecting groups (ALG) with a compound of Formula (III)

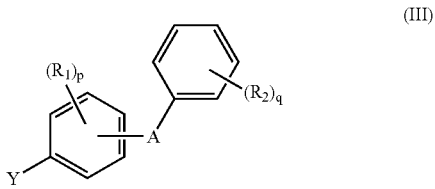

wherein Y is a metal preferably selected from alkali metals and alkaline earth metals, to yield the novel intermediate compound of Formula (IV). The intermediate compound of Formula (IV) is then treated with a glycosidation reagent (e.g., methanesulfonic acid) in the presence of a nucleophilic compound such as an alcohol, for example, to thereby remove the ALG protecting group and substitute the hydroxy group at the anomeric carbon site with an $R_3$ group as defined above, to yield the novel glycoside intermediate compound of Formula (V).

The intermediate compound of Formula (V) is then reacted with an acylating reagent to yield the novel acyl-protected intermediate compound of Formula (VI). The intermediate compound of Formula (VI) is then reduced with a reducing reagent (e.g., silyl hydrides) in the presence of an activating reagent (e.g., Lewis acids) to yield the novel intermediate compound of formula VII. Applicants have discovered that the reduction reaction in the process of the present invention, exhibits very high stereoselectivity for the desired β-aryl isomer form of the intermediate compound as shown by Formula (VII), where the diphenyl substituent bonded to the anomeric carbon is oriented in the equatorial position and is trans relative to the adjacent acyl substituent on the pyranose ring.

The intermediate compound of Formula (VII) is then reacted with an acyl protecting group removing reagent to deprotect the hydroxy groups to yield the final desired β-D-glucopyranose compound of Formula (I).

Optionally, the final compound of Formula (I) may further be treated with a complex forming reagent selected from amino acids of the type disclosed in U.S. patent application Ser. No. 10/117,914, incorporated herein by reference, such as L-phenylalanine, for example, to yield a corresponding crystalline complex of the compound of Formula (I).

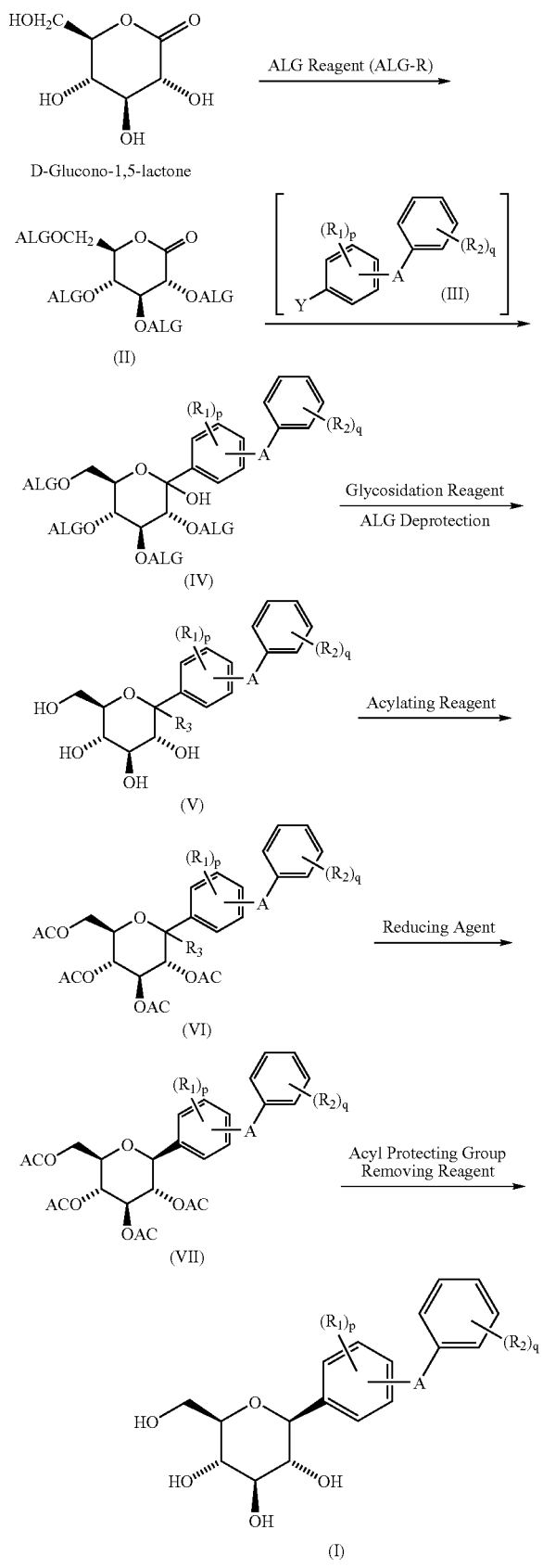

In accordance with one aspect of the present invention, novel intermediate compounds of Formula (IV) can be prepared as shown in Scheme 1 by coupling a compound of Formula (II) with a compound of Formula (III), preferably in the presence of a solvent such as toluene, for example, at reduced temperatures (e.g., −78° C.). Prior to addition of the lactone compound of Formula (II), compounds of Formula (III) may be activated for coupling with an alkyl-(alkali metal) compound such as n-BuLi and t-BuLi, for example, or an alkyl-(alkaline earth metal) compound, for example, at reduced temperatures (e.g., −78° C.) in a solvent such as THF in the presence of toluene, for example.

Compounds of Formula (II) can be prepared by treating D-glucono-1,5-lactone with an acid labile protecting group providing reagent (ALG-R) for protecting the hydroxy groups through an acid labile protecting group (ALG).

Preferred acid labile protecting groups may be selected from methoxymethyl ether, methylthiomethyl ether, 2-methoxyethoxymethyl ether, bis(2-chloroethoxy)methyl ether, tetrahydropyranyl ether, tetrahydrothiopyranyl ether, 4-methoxytetrahydropyranyl ether, 4-methoxytetrahydrothiopyranyl ether, tetrahydrofuranyl ether, tetrahydrothiofuranyl ether, 1-ethoxyethyl ether, 1-methyl-1-methoxyethyl ether, 2-(phenylselenyl)ethyl ether, t-butyl ether, allyl ether, triphenylmethyl ether, α-naphthyldiphenylmethyl ether, p-methoxyphenyldiphenyl methyl ether, trialkylsilyl ether such as trimethylsilyl ether and triethylsilyl ether, for example, isopropyldimethylsilyl ether, t-butyldimethylsilyl ether, t-butyldiphenylsilyl ether and combinations thereof.

More preferred acid labile protecting groups are selected from methoxymethyl ether, 2-methoxyethoxymethyl ether, tetrahydropyranyl ether, trimethylsilyl ether, isopropyldimethylsilyl ether, t-butyldimethylsilyl ether, t-butyldiphenylsilyl ether, and combinations thereof.

In the present invention, suitable acid labile group providing reagents may include any reagent capable of furnishing the corresponding ALG protecting groups defined above that are useful for protecting the hydroxy groups. Such reagents may include, but are not limited to, trimethylsilylchloride, trimethylsilyl trifluoromethanesulfonic acid, methoxymethylchloride, benzyloxymethylchloride, triethylsilylchloride, dihydrofuran, tetrahydropyran, and the like.

In a further aspect of the present invention, novel intermediate compounds of Formula (V) can be prepared as shown in Scheme 1 by treating the intermediate compound of Formula (IV) with a glycosidation reagent selected from an inorganic acid such as hydrochloric acid, sulfuric acid, nitric acid and the like; an organic acid such as formic acid, acetic acid, trifluoroacetic acid, methanesulfonic acid, and the like; and a Lewis acid such as boron trifluoride diethyletherate, scandium (III) trifluoromethanesulfonate, titanium (IV) isopropoxide, tin (IV) chloride, zinc (II) bromide, and zinc (II) chloride, for example, in the presence of a nucleophilic compound selected from a thiol such as an alkylthiol or an alkenylthiol, for example, and an alcohol such as methanol, butanol, ethanol, n-propanol and isopropanol, for example. The glycosidation reagent is capable of facilitating deprotection of the hydroxy groups through the removal of the acid labile protecting groups (ALG).

In a further aspect of the present invention, novel intermediate compounds of Formula (VI) can be prepared as shown in Scheme 1 by treating the intermediate compound of Formula (V) with an acylating reagent selected from an acyl derivative, an acyl halide such as acetyl chloride and the like, and an acid anhydride such as acetic anhydride, propionic anhydride, and the like which reacts with the hydroxy groups of the compound of Formula (V). The acylation reaction is preferably carried out in the presence of a base useful for promoting reactivity in the acylation reaction such as triethylamine, trimethylamine, N-N'-diisopropylethylamine (DIPEA), pyridine and 4-dimethylaminopyridine (DMAP), for example, and a reaction solvent such as toluene.

In a further aspect of the present invention, novel intermediate compounds of Formula (VII) can be prepared as shown in Scheme 1 by treatment of a compound of Formula (VI) with a reducing reagent selected from silyl hydrides including alkylsilyl hydrides, preferably a trialkylsilyl hydride such as Et$_3$SiH, for example, and preferably in the presence of an activating group including a Lewis acid such as BF$_3$.Et$_2$O, for example, and a reaction solvent such as CH$_3$CN, mixtures of CH$_3$CN/toluene, or mixtures of CH$_3$CN/dichloromethane, for example, at ambient temperatures (e.g., 15° C.).

In a further aspect of the present invention, the compounds of Formula (I) can be prepared as shown in Scheme 1 by reacting a compound of Formula (VII) under alkaline conditions with an AC protecting group removing reagent selected from a base such as NaOH, for example, to facilitate the deprotection of the hydroxy groups. The reaction is preferably carried out in the presence of a solvent selected from an alcohol such as ethanol, for example.

In accordance with the present invention, the compounds of Formula (I) can be prepared as shown in the following reaction schemes and description thereof. It will be understood that where typical or preferred process conditions (i.e. reaction temperatures, times, mole ratios of reactants, solvents, pressures, etc.) are given, other process conditions may also be used unless otherwise stated. Exemplary reagents and procedures for these reactions appear hereinafter and in the working Examples.

Protection and deprotection processes in the Reactions Scheme below may be carried out by procedures generally known in the art (see, for example, Greene, T. W. and Wuts, P. G. M., Protecting Groups in Organic Synthesis, 3$^{rd}$ Edition, 1999 [Wiley]), using the appropriate reagents described herein.

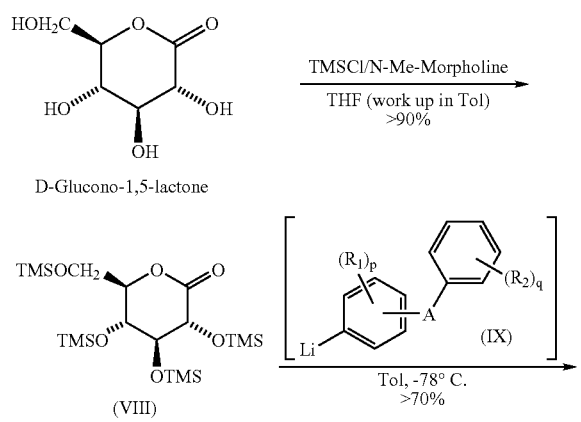

In accordance with the present invention, there is provided a method of producing the intermediate 2,3,4,6-tetra-O-(substituted silyl)-D-glucono-1,5-lactone of Formula (VIII) as shown in Scheme 2 by reacting D-glucono-1,5-lactone and an acid labile group providing reagent (ALG-R), preferably a silyl containing acid labile group providing reagent, more preferably an alkylsilyl halogen compound, most preferably a trialkylsilyl halogen compound (e.g. trimethylsilyl chloride (TMSCl)) in the presence of a base such as N-Me-morpholine, for example, and an aprotic solvent such as tetrahydrofuran, for example, to yield the intermediate compound 2,3,4,6-tetra-O-(substituted silyl)-D-glucono-1,5-lactone of Formula (VIII). Advantageously, this reaction step provides an acid labile protecting group (ALG) as a protecting group for those hydroxy groups of D-glucono-1,5-lactone that are to be preserved (i.e., remain unreacted) during subsequent reactions to produce the final product.

The resulting intermediate compound of Formula (VIII) is coupled with a lithiated anion of Formula (IX) in the presence of a reaction solvent such as toluene, for example, at a temperature of about −78° C. to yield an intermediate compound of Formula (X).

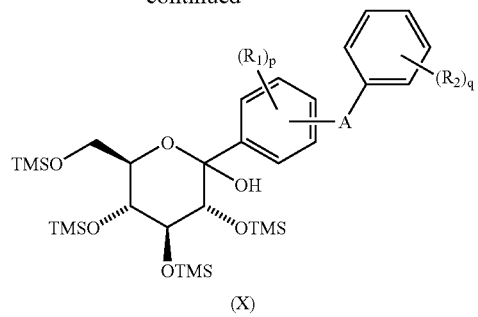

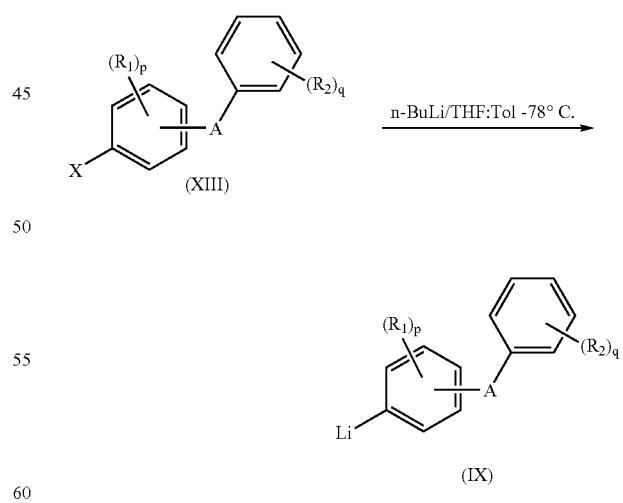

The lithiated anion of Formula (IX) is produced by reacting a starting compound of Formula (XIII), where X is selected from bromine and iodine, in the presence of a metal donor typically an alkali metal or alkaline earth metal donor such as a lithium donor, for example, preferably selected from an alkyl-(alkali metal) compound including an alkyllithium compound, preferably n-butyllithium, sec-butyllithium or t-butyllithium, and a solvent such as tetrahydrofuran:toluene or tetrahydrofuran:heptane (1:4), for example, as shown in Scheme 3.

Scheme 4

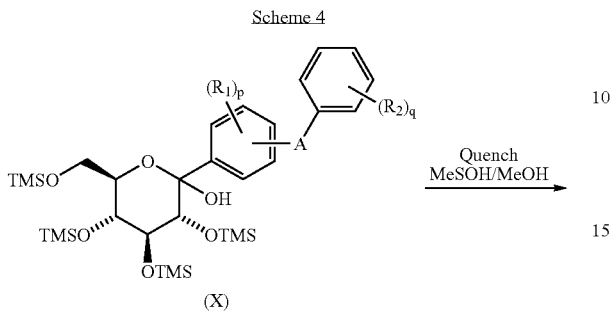

(X)

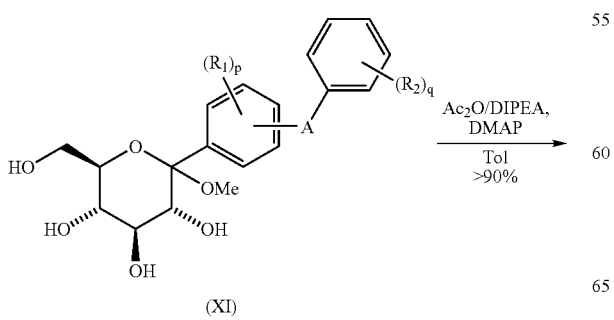

(XI)

The resulting intermediate compound of Formula (X) is then subjected to glycosidation to produce a glycoside by replacing the hydroxy group at the anomeric carbon site with a substituent selected from an alkylthio group, an alkenylthio group, an alkenyloxy group and an alkoxy group, preferably methoxy. In a preferred embodiment of the present invention, the compound of Formula (X) is treated with an acid preferably methanesulfonic acid, in the presence of an alcohol, preferably methanol, to remove the silyl containing acid labile protecting groups, the trimethylsilyl groups (TMS), and convert the anomeric carbon hydroxy group to methoxy, in accordance with Scheme 4 to yield an intermediate compound of Formula (XI).

Scheme 5

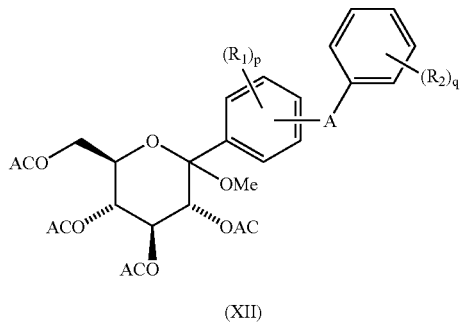

(XII)

The reactive hydroxy groups of the intermediate compound of Formula (XI) are then acylated by an acylating reagent selected from acyl derivatives, acyl halides such as acetyl chloride and the like, and acid anhydrides such as acetic anhydride, propionic anhydride, and the like. In a preferred embodiment of the present invention, the intermediate compound of Formula (XI) is reacted with acetic anhydride in the presence of N-N'-diisopropylethylamine (DIPEA) and 4-dimethylaminopyridine (DMAP), and a solvent such as toluene, for example, to yield an intermediate compound of Formula (XII) as shown in Scheme 5.

Scheme 6

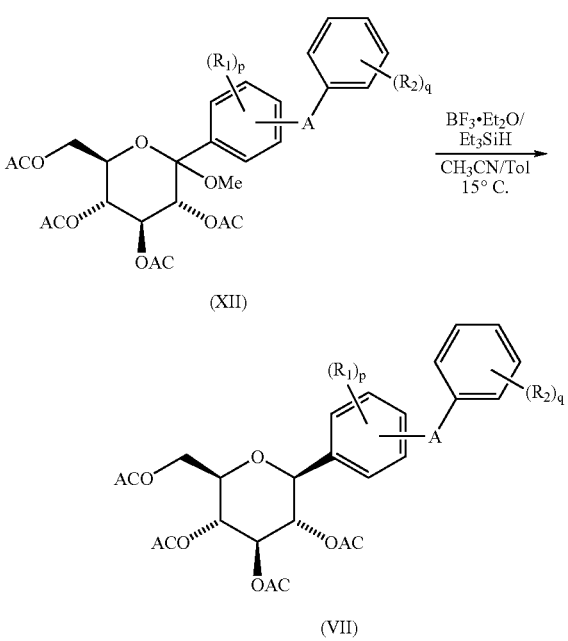

The methoxy group of the intermediate compound of Formula (XII) is then removed by treating the compound with a reducing reagent such as a silyl hydride, for example, preferably an alkylsilyl hydride and more preferably triethylsilyl hydride as shown in Scheme 6, to yield an intermediate compound of Formula (VII). The reduction reaction is preferably carried out in the presence of an activating group such as $BF_3 \cdot Et_2O$, for example, and a solvent such as CH₃CN, CH₃CN/toluene, or CH₃CN/dichloromethane, for example, at a temperature of about 15° C. The conversion of the compound of Formula (XII) as shown in Scheme 6 produces the stereospecific β-aryl form of the compound as represented by Formula (VII).

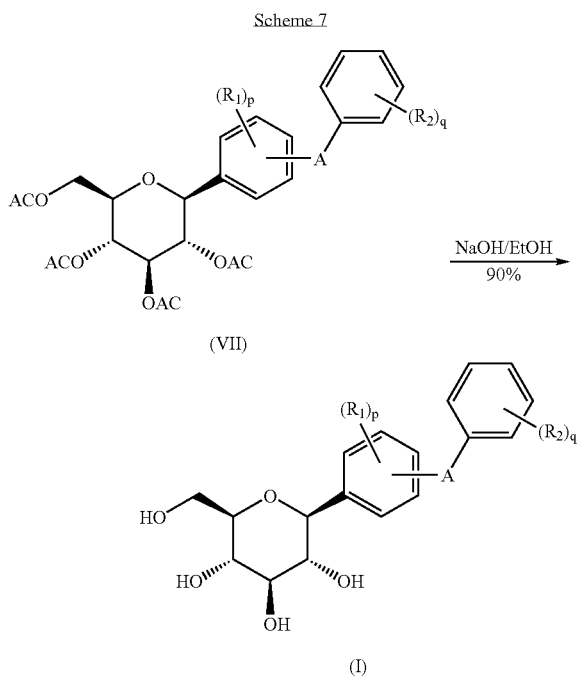

The β-aryl intermediate compound of Formula (VII) is then treated with an acyl protecting group removing reagent selected from a base, preferably sodium hydroxide to restore the hydroxy groups to yield the desired final product compound of Formula (I) as shown in Scheme 7. The acyl removing reaction is preferably carried out in the presence of a solvent such as ethanol, for example.

Optionally, the final desired product of Formula (I) may be further treated with a complex forming reagent selected from amino acids of the types disclosed in U.S. patent application Ser. No. 10/117,914, the entire disclosure of which is incorporated herein by reference, such as L-phenylalanine, for example, to yield a corresponding crystalline complex of the compound of Formula (I). The complex forming reaction is preferably carried out, for example, in the presence of a solvent such as a mixture of water and ethanol, for example.

Bases suitable for use in the final deprotection step process of the present invention include, but are not limited to, alkali metal borohydrides hydrides such as sodium borohydride, lithium aluminum hydride and the like, the alkali metal hydroxides such as sodium hydroxide, potassium hydroxide and the like, alkoxides such as sodium methoxide, sodium ethoxide, potassium tertiary butoxide and the like, sodium carbonate and potassium carbonate and amines including tertiary amines such as 4-methylmorpholine, triethylamine, N-N'-diisopropylethylamine (DIPEA), and the like. Preferred bases include sodium and potassium hydroxides. and aromatic amines such as imidazole, pyridine, and the like. Bases suitable for use in the silylation of the gluconolactone step process of the present invention include tertiary amines such as 4-methylmorpholine, triethylamine, N-N'-diisopropylethylamine (DIPEA), and the like and aromatic amines such as imidazole, pyridine, and the like.

Preferred bases include tertiary amine bases with 4-methylmorpholine being an especially preferred base.

Aprotic reaction solvents suitable for use in the aryllithium coupling and the glycoside reduction processes of the present invention include, but are not limited to, an ether such as dioxane, tetrahydrofuran, and the like, aromatic hydrocarbons such as benzene, toluene, xylene, and the like, esters such as ethyl acetate, and the like, halogenated hydrocarbons such as chloroform, dichloromethane, and the like, nitriles such as acetonitrile, and the like, amides such as N,N-dimethylformamide, N,N-dimethylacetamide, and the like, and sulfoxides such as dimethylsulfoxide, and the like. Preferred aprotic solvents for coupling reaction are toluene and tetrahydrofuran, a 4:1 mixture of these solvents being an especially preferred medium. Whereas, the preferred aprotic solvents for the glycoside reduction step being CH₃CN.

Most importantly, it has been found that acid labile protecting groups described above, especially those containing a silyl group, compared with other protecting groups such as benzyl groups, enable the process to be conducted in a one-pot operation with the formation of fewer intermediate compounds, which must be isolated. The acid labile protecting groups preferably react with the hydroxy groups of D-glucono-1,5-lactone and remain preferentially bonded thereto until it is desired to remove the same.

Acid labile protecting groups, especially the trimethyl silyl group of the present invention greatly facilitates large-scale synthesis as a result of lower costs and use of readily available starting materials. Moreover, the use of this acid labile protecting groups in the method of the present invention provides a safer synthesis process which minimizes hazardous reaction conditions while enhancing improved stereoselectivity (35:1) and product purity over prior art processes using benzyl protecting groups.

The amount of the acid labile protecting group providing reagent is typically greater than the stoichiometric amount and is desirably sufficient to protect all of the targeted hydroxy groups of D-glucono-1,5-lactone (the hydroxy groups which are not to react during the synthesis). Preferably a molar ratio of greater than 4.0, more preferably about 6.0 is desirable. The protective group reaction is preferably carried out at temperatures not exceeding 10° C.

In a preferred embodiment of the present invention, the intermediate compounds of Formula (VIII) as shown in Scheme 2, are produced by first mixing D-glucono-1,5-lactone and an aprotic solvent followed by the addition of the base, preferably about 5 to 8 molar equivalents based on the amount of D-glucono-1,5-lactone. The acid labile group providing reagent is then added, preferably in an amount of 6 molar equivalents to yield the intermediate compound of Formula (VIII) which is then reacted with the lithiated anion of Formula (IX).

The formation of the intermediate compound of Formula (VIII) is typically conducted at a temperature of from about 0° C. to 50° C., preferably about 35° C. until the reaction is completed, typically about 5 hours. The reaction mixture is then cooled, diluted with a solvent, neutralized with a buffer such as sodium dihydrogen phosphate, for example, washed and distilled to obtain the intermediate compound of Formula (VIII).

The intermediate compound of Formula (VIII) is then reacted with the lithiated anion of Formula (IX), which is obtained by reacting a solution of a compound of Formula (XIII) as shown in Scheme 3 in an aprotic solvent with an alkyllithium compound preferably an n-alkyllitthium compound, more preferably n-butyllitthium at slightly greater than a stoichiometric amount at reduced temperatures typically less than –70° C. in an inert atmosphere, to yield the intermediate compound of Formula (X).

The intermediate compound of Formula (X) is reacted with a glycosidation reagent such as sulphuric acid, hydrochloric acid, methanesulfonic acid, p-toluenesulfonic acid, and trifluoromethanesulfonic acid, for example, preferably methanesulfonic acid, in the presence of a nucleophilic compound such as a lower alcohol, for example, preferably methanol, butanol, ethanol, n-propanol, isopropanol and the like. The reaction is conducted at a temperature of about 40° C. The reaction solution is then quenched with a quenching agent such as sodium bicarbonate, for example, at a temperature of less than 30° C. to yield the intermediate compound of Formula (XI) as shown in Scheme 4.

The intermediate compound of Formula (XI) is converted to the acylated derivative by an excess amount of an acyl donor such as acetic anhydride, for example. The amount of the acyl donor should be sufficient to provide maximum conversion of the hydroxy groups, typically from about 4 to 6 equivalents based on the amount of the compound of Formula (XI). The reaction is conducted in the presence of excess N-N'-diisopropylethylamine (DIPEA) and a catalyst such as 4-dimethylaminopyridine (DMAP), for example. The temperature of the reaction is generally maintained at less than about 35° C. until the reaction is completed. The reaction is then quenched by reducing the reaction pH to about 3 or less with the addition of an acid such as phosphoric acid, for example, as shown in Scheme 5.

At this step of the process, compound of Formula (XII) is treated with a reducing reagent to remove the methoxy group from the anomeric carbon site on the glucopyranoside ring. Applicants have determined that silyl-based reducing reagents, preferably trialkylsilyl hydrides, more preferably triethylsilyl hydride in the presence of an acid are preferred to reduce the glucopyranoside compound of Formula (XII) to the glucopyranose compound of Formula (VII) with exceptional stereoselectivity, about 98% and the yield, typically about 80–90%. The reduction reaction is preferably conducted in the presence of borontrifluoride-etherate ($BF_3 \cdot Et_2O$) and acetonitrile ($CH_3CN$) as shown in Scheme 6. Most significantly, unlike the corresponding benzyl protected intermediates, the use of acetyl protecting groups enabled the reduction step to be performed without the use of a highly hindered silylhydride under non-crygenic conditions with exceptional stereoselectivity, The intermediate compound of Formula (VII) is then treated with a base as previously described, such as sodium hydroxide or lithium hydroxide, for example, in the presence of a solvent such as a lower alcohol (e.g., ethanol), for example. The final resulting product of Formula (I) is obtained. Optionally, the resulting compound of Formula (I) may be reacted with a complex forming reagent selected from amino acids such as L-phenylalanine, for example, in a suitable solvent such as a lower alcohol and water, for example, to obtain the corresponding crystalline complex such as the L-phenylalanine complex, for example, of the compound of Formula (I).

In a further aspect of the present invention, the processes described above may be used to prepare the C-aryl glucoside compounds of Formula (I) including 1-C-(4'-ethyldiphenyl-methane-3-yl)-β-D-glucopyranose, 1-C-(6-methyl-4'-(methylthio)diphenylmethane-3-yl)-β-D-glucopyranose, 1-C-(6-chloro-4'-ethoxydiphenylmethane-3-yl)-β-D-glucopyranose, and complexes thereof.

In a more preferred embodiment of the present invention, 1-C-(4'-ethyldiphenylmethane-3-yl)-β-D-glucopyranose is produced employing essentially the same steps as described above. In particular, the lithiated anion of Formula (IX) wherein $R_1$ is hydrogen, $R_2$ is 4'-ethyl and A is —$CH_2$— which reacts with the 2,3,4,6-tetra-O-(substituted silyl)-D-glucono-1,5-lactone of Formula (VIII), is formed by reacting 3-bromo-4'-methyldiphenylmethane of Formula (XIII) with an n-alkyl lithium.

In a more preferred embodiment of the present invention, 1-C-(6-methyl-4'-(methylthio)diphenylmethane-3-yl)-β-D-glucopyranose is produced employing essentially the same steps as described above. In particular, the lithiated anion of Formula (IX) wherein $R_1$ is 4-methyl, $R_2$ is 4'-(methylthio) and A is —$CH_2$—, which reacts with the 2,3,4,6-tetra-O-(substituted silyl)-D-glucono-1,5-lactone of Formula (VIII), is formed by reacting 3-bromo-4-methyl-4'-(methylthio) diphenylmethane of Formula (XIII) with an n-alkyl lithium.

In a more preferred embodiment of the present invention, 1-C-(6-chloro-4'-ethoxydiphenylmethane-3-yl)-β-D-glucopyranose is produced employing the same steps as described above. In particular, the lithiated anion of Formula (IX) wherein $R_1$ is 4-chloro, $R_2$ is 4'-ethoxy and A is —$CH_2$—, which reacts with the 2,3,4,6-tetra-O-(substituted silyl)-D-glucono-1,5-lactone of Formula (VIII), is formed by reacting 3-bromo-4-chloro-4'-ethoxydiphenylmethane of Formula (XIII) with an n-alkyl lithium.

The starting compound of Formula (XIII) is known in the art and may be readily prepared using standard procedures known to those of ordinary skill in the art.

The following examples are offered only to illustrate the invention, and should not be interpreted as a limitation thereon. For example, optimum reaction conditions may vary with the particular reactants or solvents used, however such reaction conditions may be determined by one of ordinary skill in the art through routine optimization procedures.

EXAMPLE 1

Preparation of 2,3,4,6-tetra-O-trimethylsilyl-1-C-(6-methyl-4'-(thiomethyl)diphenylmethan-3-yl)-α-D-glucopyranose

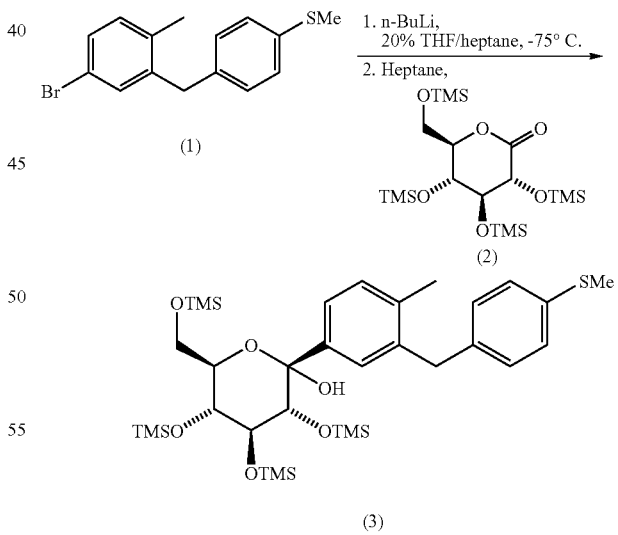

In a one-necked, 1 L round bottom flask, an aryl bromide compound (1) (20.7 g, 67.4 mmol, 1.1 equiv) was dissolved in tetrahydrofuran (THF) (61 mL) and heptane (245 mL), and cooled to −78° C. to generate a precipitate. 2.3 M n-BuLi (29.3 mL, 67.4 mmol) was added dropwise to the heterogenous reaction mixture over 20 minutes to yield a reddish color. After 30 minutes, the reaction mixture was transferred to a one-necked 2-L flask containing a trimethylsilyl lactone compound (2) (29.5 g, 63.2 mmol, 1 equivalent) and heptane (306 mL) at −78° C. to yield a cloudy mixture without any precipitate. The reaction mixture was removed from the cold bath, quenched with 1% AcOH (290 mL), and thereafter transferred to a separatory funnel. 200 ML of ethyl acetate (EtOAc) was added and the layers separated. The organic layer was washed with water (1×200 mL) and brine (2×200 mL). The aqueous layer was back-extracted with EtOAc. The TMS protected compound (3) was no longer detected through TLC analysis (ca. 750 mL EtOAc). The combined organic layers were dried over $MgSO_4$, filtered and concentrated to provide 48 g of a yellow foamy oil, which was stirred and dried under high vacuum for about 0.5 hour. The resulting TMS protected compound (3) was used for the next example.

EXAMPLE 2

Preparation of Methyl-1-C-(6-methyl-4'-(thiomethyl)diphenylmethan-3-yl)-α-D-glucopyranose

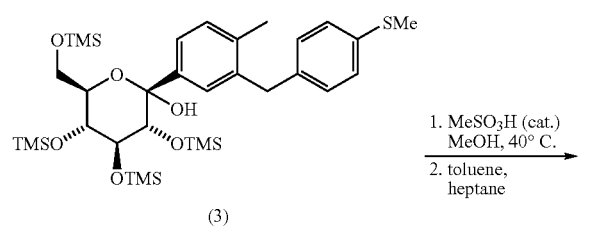

(3)

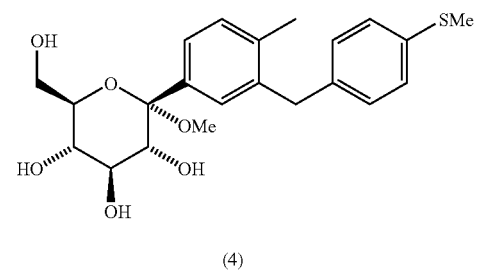

(4)

The TMS protected compound (3) (48 g) from Example 1 was dissolved in MeOH (196 mL) and methanesulfonic acid (200 μL) was added. The resulting solution was warmed to 40° C. for about 20 minutes. Thereafter, the solution was cooled to room temperature and concentrated. The residue was dissolved in EtOAc (200 mL), washed with saturated aqueous $NaHCO_3$ (2×100 mL) and brine (2×100 mL). The combined aqueous layers were back-extracted with EtOAc (2×100 mL), and the combined organic layers were dried over $Na_2SO_4$, filtered and concentrated. The residue was dried under high vacuum overnight, and then dissolved in toluene (ca. 75 mL) at 60° C. The resulting mixture was added dropwise to a round bottom flask containing 450 mL of heptane to yield a white precipitate. The mixture was stirred for about 3 hours at room temperature, and then filtered to yield 27 g of compound (4) as a white solid. Through HPLC analysis, the white solid was determined to be 87% pure. An HPLC analysis was performed on the filtrate, which indicated the absence of the compound (4).

EXAMPLE 3

Preparation of 1-C-(6-methyl-4'-(thiomethyl)diphenylmethan-3-yl)-β-D-glucopyranose

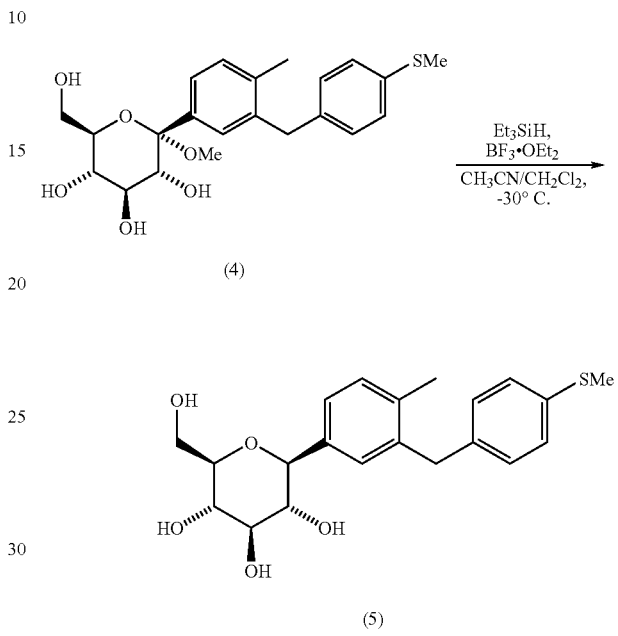

The compound (4) from Example 2 was divided in half to prepare two reaction mixtures. In a first 1-L round bottom flask, the compound (4) (13 g, 30.9 mmol, 1 equiv) was dissolved in $CH_2Cl_2$ (86 mL) and $CH_3CN$ (223 mL) and cooled to −20° C., which caused the starting material to precipitate. With stirring, $Et_3SiH$ (9.9 mL, 61.8 mmol, 2 equiv) was added followed by $BF_3 \cdot OEt_2$ (5.9 mL, 46.4 mmol, 1.5 equiv). In a second 1-L round bottom flask, a separate reaction mixture was prepared by dissolving 11 g of the compound (4) in $CH_2Cl_2$ (73 mL), $CH_3CN$ (190 mL), $Et_3SiH$ (8.4 mL), and $BF_3 \cdot OEt_2$ (5.0 mL). The reaction mixtures were allowed to stand for about 30 minutes to yield orange and homogenous solutions. Each of the reaction mixtures were quenched with saturated aqueous $NaHCO_3$ (ca. 200 mL), and then warmed to room temperature. The reaction mixtures were combined, and the organic solvents were removed under reduced pressure. 500 ML of EtOAc were added and the layers were separated in a separatory funnel. The organic layer was washed with saturated aqueous $NaHCO_3$ (2×300 mL) and brine (2×200 mL). The combined aqueous layers were back-extracted with EtOAc until no traces of the desired product were observed in the washes via TLC analysis (ca. 600 mL EtOAc). The combined organic layers were dried over $MgSO_4$, filtered and concentrated to provide 23 g of a compound (5) as a pale yellow foam. Amorphous compound (5) was purified by conversion to its crystalline derivative tetraacetate (6) and hydrolysis as described below in Examples 4 and 5.

EXAMPLE 4

Preparation of 2,3,4,6-tetra-O-acetyl-1-C-(6-methyl-4'-(thiomethyl)diphenylmethan-3-yl)-β-D-glucopyranose

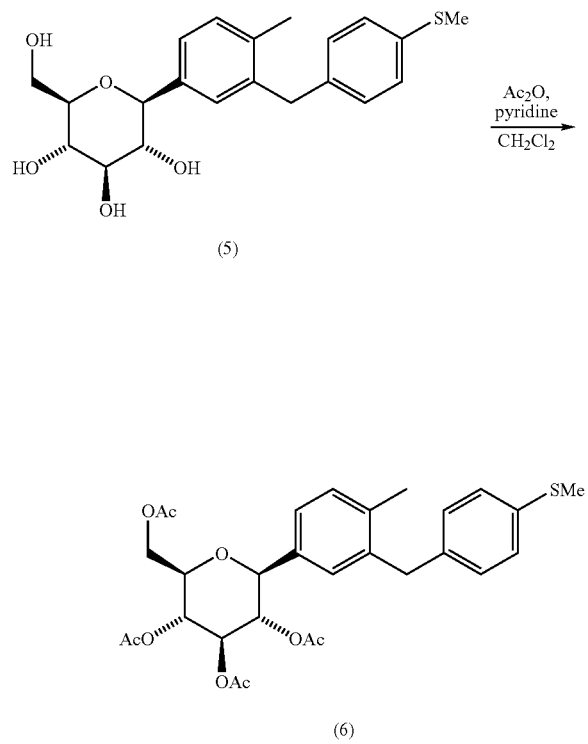

(5)

(6)

The compound (5) (8.3 g, 21.3 mmol, 1 equiv) from Example 3 was dissolved in CH₂Cl₂ (53 mL) and pyridine (17 mL, 210 mmol, 9.9 equiv). Acetic anhydride (20 mL, 212 mmol, 10 equiv) was added to the reaction mixture, and thereafter 4-dimethylaminopyridine (DMAP) (130 mg, 1.1 mmol, 0.05 equiv). The reaction mixture was stirred for about 50 minutes. Water (200 mL) and CH₂Cl₂ (200 mL) were added, and the layers were separated in a separatory funnel. The organic layer was washed with 1 N HCl (3×200 mL) and brine (2×100 mL). The combined aqueous layers were back-extracted with CH₂Cl₂ until TLC analysis showed that the desired product was no longer present in the extracts. The combined organic layers were dried over MgSO₄, filtered and concentrated to yield 11 g of a pale yellow solid. The resulting product was purified via recrystallization using EtOAc/hexane by dissolving the solid in EtOAc (48 mL) at 50° C. and adding hexane (119 mL) to the mixture where the mixture was slowly cooled to room temperature then to 4° C. overnight. After recrystallization, 7.7 g of compound (6) as a white solid was obtained (100% pure via HPLC).

EXAMPLE 5

Preparation of 1-C-(6-methyl-4'-(methylthio)diphenylmethane-3-yl)-β-D-glucopyranose

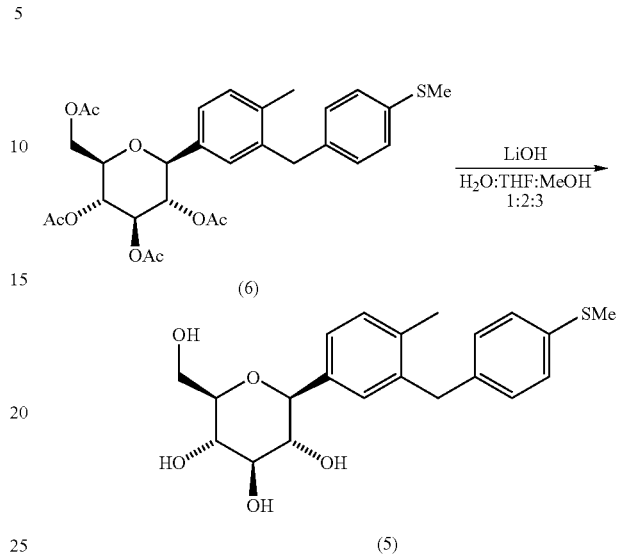

(6)

(5)

Compound (6) (22.3 g, 39.9 mmol, 1 equiv) from Example 4 was dissolved in THF/MeOH/H₂O and stirred at room temperature. LiOH.H₂O (1.65 g, 39.3 mmol, 1 equiv) was added to the reaction mixture to yield a light yellow solution. The reaction mixture was maintained at room temperature for about 5.2 hours and was then concentrated under reduced pressure. The residue was dissolved in EtOAc (300 mL), and thereafter, saturated aqueous NaHCO₃ (200 mL) was added. The layers were separated, and the organic layer was washed with NaHCO₃ (1×200 mL) and brine (1×200 mL). The aqueous layers were back-extracted with EtOAc (3×300 mL). The combined organic layers were dried over MgSO₄, filtered and concentrated to yield 15.5 g of 1-C-(6-methyl-4'-(methylthio)diphenylmethane-3-yl)-β-D-glucopyranose (5) as a white, glassy solid.

EXAMPLE 6

Preparation of 3-bromo-2-methyl-4'-(methylthio)diphenyl methane 100.0 G of o-toluic acid was suspended in 115 mL of methylene chloride in a reaction vessel to form a slurry. 2.6 g of iron powder was added to the slurry followed by the addition of 143.1 g of bromine over 40 minutes while maintaining the reaction temperature at about 30° C.

The resulting reaction mixture (151.0 g) was added to 450 mL of ethanol under slight stirring, and followed by heating to a temperature of from about 70° C. to 80° C. The reaction mixture was then cooled to ambient temperature. Crystals of 3-bromo-2-methyl-benzoic acid were filtered off by suction and washed with an aqueous ethanol solution.

A separate vessel was charged with 770 mL of methylene chloride. 100.0 of 3-bromo-2 methyl-benzoic acid was added to the reaction vessel under light stirring. 70.3 g of oxalychloride was added to the reaction vessel with 0.3 mL of dimethylformamide under stirring for 24 hours under ambient temperature to produce 5-bromo-2 methyl-benzoyl chloride which was then dissolved in 500 mL of methylene chloride. 57.8 g of thioanisole was added to the reaction vessel, which was cooled to 10° C. followed by the addition of a first charge of 12.4 g of aluminum chloride under stirring for 15 minutes. Thereafter four successive charges of aluminum chloride were added at each time the reaction temperature reached 10° C. The reaction mixture was then poured onto 300.0 g of ice and 435 mL of 2N hydrochloric acid and stirred for one hour. The aqueous and organic layers were then separated and the organic layers were washed with 210 mL of 2N hydrochloric acid and twice with 160 mL portions of sodium bicarbonate solutions.

The methylene chloride and water were then removed followed by the addition of 270 mL of ethanol. The resulting solution was cooled to 0° C. to obtain crystals of 3-bromo-2-methyl-4'-(methylthio)diphenylmethane.

The product (5) produced as described above was then treated in substantially the same manner as described in Example 12 to obtain 1-C-(6-methyl-4'-(methylthio)diphenylmethane-3-yl)-β-D-glucopyranose and L-phenylalanine complex.

EXAMPLE 7

Preparation of 2,3,4,6-tetra-O-(trimethylsilyl)-D-glucono-1,5-lactone 700.0 g of D-glucono-1,5-lactone and 7 L of tetrahydrofuran along with 3185.0 g of 4-methylmorpholine were added to a 60 L reaction vessel which was maintained at less than 5° C. 2590 g of trimethylsilyl chloride were added to the vessel and the contents were maintained at 35° C. for 5 hours. Thereafter, the vessel was cooled to 0° C. 10.5 L of toluene and 14 L of water were added to the vessel. The aqueous and organic phases were separated and the organic phase was washed with aqueous dihydrogen phosphate monohydrate to remove excess base and bring the pH of the solution to 7 to 8.

After washing with water, the organic phase was distilled under reduced pressure (23 in. Hg) at 50° C. until the moisture content of the organic phase was no greater than 0.05% and a concentration of about 1.0 g/10 mL of the title compound was obtained.

EXAMPLE 8

Preparation of 3-Bromo-4'-ethyldiphenylmethane

A. 3-Bromo-4'-ethylbenzylhydrol

Dry Mg turnings (4.4 g, 0.178 mol) under Ar were stirred overnight whereupon 100 mL of dry $Et_2O$ was added followed by addition over 1 hr of p-bromoethylbenzene (22 g, 0.119 mol) in 20 mL of $Et_2O$. (In the event the reaction did not start, 0.5 ml of 1,2-dibromoethane was added). After stirring overnight, m-bromobenzaldehyde (11 g, 0.06 mol) in 20 mL of $Et_2O$ was slowly added. The resulting light solution was monitored by HPLC over the period of from about 4 to 6 hr to determine when complete. The reaction, after quenching with saturated aq. $NH_4Cl$, was extracted 3 times with EtOAc. The combined organic layers were washed with brine, dried over $Na_2SO_4$ and concentrated using a rotary evaporator. The resulting yellow oil was chromatographed on silica gel using 5% EtOAc/hexane to elute nonpolar impurities and 7 to 9% EtOAc/hexane to elute 12.4 g (71%) of 3-bromo-4'-ethylbenzhydrol as a light yellow oil.

B. 3-Bromo-4'-ethyldiphenylmethane

To a stirred −30° C. solution of Part A 3-bromo-4'-ethylbenzhydrol (12.4 g, 0.0426 mol) in 120 mL of MeCN was added $BF_3Et_2$ 0 (6.04 g, 0.0426 mol) followed by $Et_3SiH$ (9.9 g, 0.852 mol). The dark reaction after stirring for 1 hr at −30° C. was warmed slowly to −5° C. When complete by TLC, the reaction was quenched by addition of saturated aq. $K_2CO_3$. After addition of 100 mL of $H_2O$, the mixture was extracted 3 times with $Et_2O$. The combined organic layers were washed with brine, dried over $Na_2SO_4$. After concentration using a rotary evaporator, 3-bromo-4'-ethyldiphenylmethane (11.17 g, 95%) was obtained as a light yellow oil that was used without further purification.

EXAMPLE 9

Preparation of Methyl-1-C-(4'-ethyldiphenylmethan-3-yl)-α-D-glucopyranoside 895.0 g of 3-Bromo-4'-ethyldiphenylmethane (obtained from Austin Chemicals of Chicago, Ill.), 1.6 L of tetrahydrofuran and 6.5 L of toluene were added to a 20 L reaction vessel under an inert nitrogen atmosphere and cooled to −80° C. 1.4 L of n-butyllithium was added over 30 minutes to the reaction vessel while maintaining the reaction temperature at about −80° C. The reaction mixture was stirred while maintaining the inert atmosphere until the reaction was completed to thereby obtain 3-lithium-4'-ethyldiphenylmethane.

The reaction mixture was combined with the solution of 2,3,4,6-tetra-O-(trimethylsilyl)-D-glucono-1,5-lactone prepared in Example 7 and stirred for 30 minutes at −80° C. in an inert atmosphere.

The lithiated intermediate compound prepared above was combined over 30 minutes with a solution of 443.0 g (4.61 mol) of methanesulfonic acid and 7.2 L of methanol while maintaining the temperature of the reaction vessel at less than −60° C. to produce methyl-1-C-(4'-ethyldiphenylmethane-3-yl)-α-D-glucopyranoside at a yield of 76.9%.

EXAMPLE 10

Preparation of methyl-2,3,4,6-tetra-O-acetyl-1-C-(4'-ethyldiphenylmethan-3-yl)-α-D-glucopyranose 550 mL of a 60.2 mg/mL solution of methyl-1-C-(4'-ethyldiphenylmethane-3-yl)-α-D-glucopyranoside in toluene prepared in accordance with Example 9 and 0.1 g of 4-(dimethylamino)pyridine were added to the reaction vessel under stirring in an inert nitrogen atmosphere followed by the addition of 84 mL of N,N'-diisopropylethylamine (DIPEA) and 40.9 mL of acetic anhydride while maintaining the temperature at no greater than about 35° C. The reaction mixture was stirred for about 4 to 7 hours to produce methyl-2,3,4,6-tetra-O-acetyl-1-C-(4'-ethyldiphenylmethan-3-yl)-α-D-glucopyranoside.

The reaction mixture was then quenched with 330 ml of 17% phosphoric acid until the pH of the lower aqueous phase was no greater than 3. The lower aqueous phase containing excess acid was sent to waste.

The rich upper organic phase was washed with 325 mL of water. The organic phase was concentrated at atmospheric pressure to produce methyl-2,3,4,6-tetra-O-acetyl-1-C-(4'-ethyldiphenylmethan-3-yl)-α-D-glucopyranoside.

Thereafter 232 mL of acetonitrile in 1.5 mL of water (1 eq.) was added to the reaction vessel at a temperature of no greater than 15° C. Thereafter 40 mL of triethylsilane and 21.1 mL of boron trifluoride etherate were added to the reaction vessel over 20 minutes while maintaining the reaction temperature at no greater than 25° C., and stirring the reactants over 4–7 hours, to thereby obtain 2,3,4,6-tetra-O-acetyl-1-C-(4'-ethyldiphenylmethan-3-yl)-β-D-glucopyranose at a yield of 86%.

EXAMPLE 11

Preparation of 1-C-(4'-ethyldiphenylmethan-3-yl)-β-D-glucopyranose 2.0 g of 2,3,4,6-tetra-O-acetyl-1-C-(4'-ethyldiphenylmethane-3-yl)-β-D-glucopyranose prepared in accordance with Example 10 was added to 20 mL of ethanol at a temperature of 20° C. followed by the addition of 0.83 g of lithium hydroxide monohydrate. The mixture was stirred overnight followed by the addition of 10 mL of water. The pH was adjusted to 5.5 by the addition of 2 mL of 6N hydrochloric acid.

The resulting solution was evaporated to 5 mL of volume (in mostly ethanol) to produce 1-C-(4'-ethyldiphenylmethane-3-yl)-β-D-glucopyranose.

EXAMPLE 12

Preparation of 1-C-(4'-Ethyldiphenylmethane-3-yl)-β-D-glucopyranose L-phenylalanine Complex 1-C-(4'-ethyldiphenylmethane-3-yl)-β-D-glucopyranose in solution as prepared in accordance with Example 11 was combined with 0.63 g of L-phenylalanine and 45 mL of water. The mixture was heated to 83° C. and then cooled under agitation to 60° C. Seed crystals of L-phenylalanine complex were added for every 2° C. drop in temperature until the originally clear solution became a thin slurry with evident solid presence.

The resulting slurry was agitated for four hours at 40° C. to 42° C. and then at ambient temperatures over night. The slurry was then filtered, washed and dried at 40° C. to yield 1-C-(4'-ethyldiphenylmethane-3-yl)-β-D-glucopyranose-L-phenylalanine complex.

EXAMPLE 13

Preparation of 1-C-(6-Chloro-4'-ethoxydiphenyl-methane-3-yl)-β-D-glucopyranose

Using essentially the same procedures as described in Examples 9–12 except that 5-bromo-2-chloro-4'-ethoxydiphenylmethane is substituted for 3-bromo-4'-ethyldiphenylmethane, 1-C-(6-chloro-4'-ethoxydiphenylmethane-3-yl)-β-D-glucopyranose and the corresponding L-phenylalanine complex thereof are obtained.

Alternatively, the 1-C-(6-chloro-4'-ethoxydiphenylmethane-3-yl)-β-D-glucopyranose may be prepared according to the methods described in Examples 14 through 21.

EXAMPLE 14

Preparation of 2-chloro-5-bromobenzoic Acid Chloride

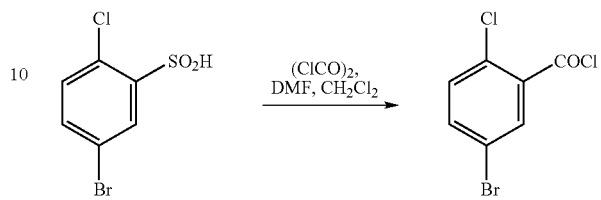

8.00 kg 2-chloro-5-bromobenzoic acid was suspended in 80.00 L methylene chloride (KF of methylene chloride <0.1% $H_2O$) and 0.02 L of DMF added at 20° C. 5.18 Kg oxalyl chloride were slowly added and the internal temperature maintained below 25° C. The addition was slightly exothermic; gas evolution of HCl and $CO_2$ occurred. The reaction was run at 20–25° C. overnight; a clear solution was obtained. The mixture was concentrated in vacuum to an oily residue and degased at 40° C. in vacuum. Yield of 2-chloro-5-bromobenzoic acid chloride: 8.63 kg (33.98 mol, yield 100.0%)

EXAMPLE 15

Preparation of 2-chloro-5-bromo-4'-ethoxybenzophenone

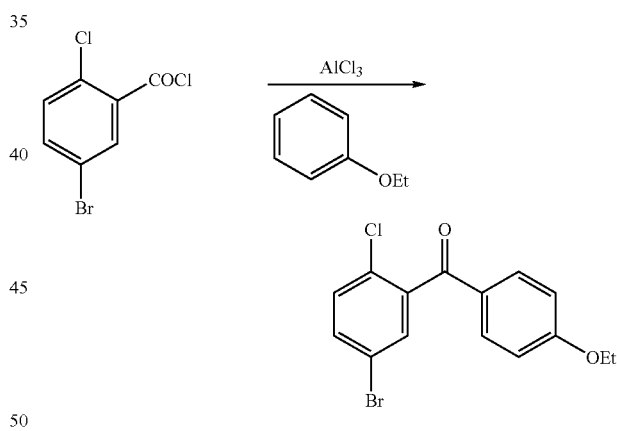

65.32 L methylene chloride were charged to a reactor and then 7.44 kg aluminium chloride added. The reaction mixture was cooled to 0° C. and 6.81 kg phenetol slowly added while maintaining temperature at 0–5° C. After complete addition, the mixture was cooled to 0° C. and agitated 15–20 min before proceeding.

In a separate reactor 14.16 kg 2-chloro-5-bromobenzoic acid chloride were diluted with 25.49 L methylene chloride. A sample was taken for HPLC analysis. This solution was added to the mixture prepared above at such a rate that the temperature is maintained at 0–5° C. A red solution was obtained. The mixture was agitated at 0–5° C. and samples taken for HPLC and quenched with MeOH every 45 min. The reaction was considered complete if methyl ester was below 1 AP (area percent purity). The reaction mixture was quenched by adding it with vigorous agitation and cooling to a mixture of 32.66 L 2M HCl and 16.33 kg ice. The temperature was maintained below 25° C. The mixture was agitated at 20–25° C. for 20 min and then the phases separated. The organic phase was slightly turbid. The organic phase was washed with 26.13 L of 2M HCl, and the combined aqueous phases extracted with 13.06 L methylene chloride. The combined organic layers from the above steps were washed twice with 39.19 L sat. Na-bicarbonate solution after stirring each time for at least 30 min. The combined organic layers were then extracted with 13.06 L of methylene chloride. The combined organic layers were washed finally with 19.6 L brine. The organic phase was concentrated to dryness in vacuum and the residue dissolved at 50–60° C. with 32.66 L of ethanol. 13.06 L water were slowly added, at which point crystallization began.

The slurry was agitated at 20–25° C. for 1 h then another 6.53 L water added with continued agitation for 1 h. The precipitate was collected and the cake washed with a total of 23.52 L water/ethanol (2:1, precooled to −5° C.) in portions. The product was dried to a final water content of less than 0.1%, with a yield of 17.31 kg (91.3%) of the title benzophenone. The product was a mixture of para- and ortho-isomer (ratio 93:7). The undesired ortho-isomer was removed in the subsequent reaction step.

EXAMPLE 16

Preparation of 2-chloro-5-bromo-4'-ethoxydiphenylmethane

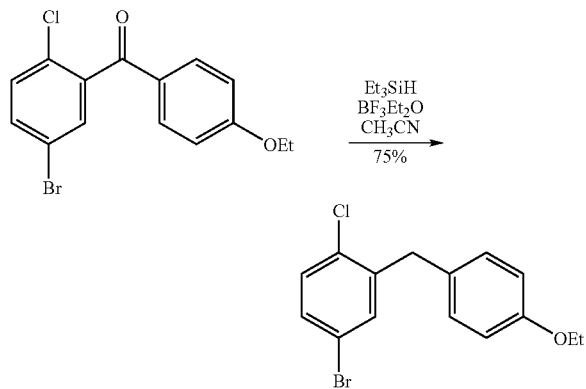

10.81 Kg of 2-chloro-5-Bromo-4'-ethoxybenzophenone were dissolved in 109.72 L acetonitrile and the solution cooled to 10° C. 9.99 Kg triethylsilane were added, and a sample taken for HPLC. 12.18 Kg boron trifluoride etherate were slowly added and the reaction temperature maintained below 20° C. (Generally, after addition the temperature may increase to 20–25° C. without heating.) The reaction mixture was agitated at this temperature with casual cooling, and a sample taken for HPLC analysis every hour until the reaction was complete. During the reaction a precipitate was formed. The reaction was considered complete if the amount of remaining starting material was less than 0.1 AP (after 4–6 h). 47.01 L MTBE were added to the reaction mixture, and the mixture washed twice with 47 L sat. Na-bicarbonate solution. The combined aqueous phases were extracted with 15.67 L MTBE; the combined organic phases were washed with 15.67 L brine. The organic phase was concentrated to dryness in vacuo. The semisolid residue was then dissolved in 21.55 L ethanol with heating. The solution was seeded and allowed to crystallize while cooling overnight to 20–25° C. At the end of this step, the slurry was agitated at 0° C. for 1 h. The precipitate was collected and the cake washed twice with 3.92 L precooled ethanol (−5–0° C.). The product was dried in vacuum at 40° C. to constant weight (final water content: KF<0.08%) Yield: 7.80 kg of the title compound (23.97 mol, 75.3%).

EXAMPLE 17

Preparation of Methyl-1-C-(2-chloro-4'-ethoxy-diphenylmethan-3-yl)-α-D-glucopyranose

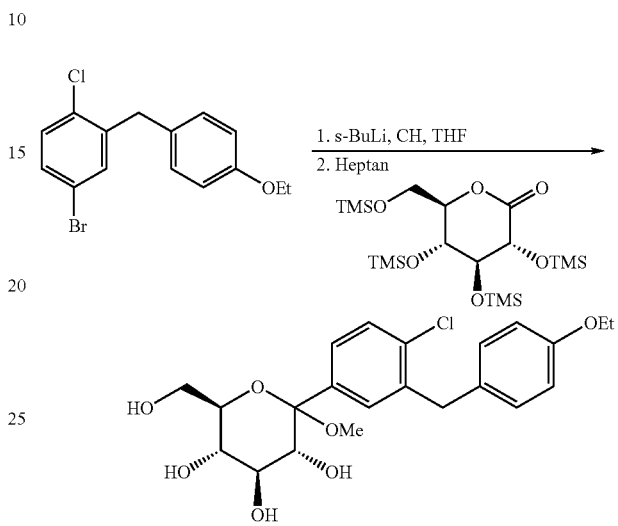

A solution of 11.97 kg 2-Chloro-5-bromo-4'-ethoxy-diphenylmethane was charged to a first reactor containing 120 L THF. A sample was taken for HPLC and then the solution was cooled to −78° C. In a second reactor 17.16 kg of 2,3,4,6-tetra-O-trimethylsilyl-D-gluconolactone were dissolved in 87 L of heptane and the solution cooled to −78° C. To the first reactor was added 23.15 kg s-BuLi (12% in cyclohexane) at such a rate that the reaction temperature did not exceed −68° C. After complete addition the mixture was agitated at −78° C. for 1 h, then a sample was taken for HPLC. Care was taken to avoid contact with humidity during sampling. (At this point, if the content of starting materials is determined to be less than 3 AP, the reaction may be continued to the next step; or if not, additional s-BuLi may be necessary.) The content of reactor one was added via a cooled line (−78° C.) to the cooled second reactor (−78° C.) at such a rate that the temperature did not exceed −68° C. After complete addition, the mixture in the second reactor was agitated at −78° C. for 30 min, then a sample taken for HPLC. Sampling was repeated every hour until completeness. The reaction was considered complete if no changes in AP were observed in two consecutively taken samples. The mixture was warmed to −40° C., then 100 L water added very carefully. The mixture was agitated vigorously for 10 min and then the phases separated, and the aqueous phase extracted with 35 L MTBE. The combined organic phases were washed with 35 L brine. The organic phase was then concentrated to an oily residue and degassed carefully at 40° C. in vacuum to remove all volatiles. The oily residue was dissolved in 100 L methanol and 1.72 kg methanesulfonic acid slowly added. (At this stage, the reaction temperature may increase to 30° C.). The reaction mixture was agitated at 20–25° C. for about 12 h, then heated to 40° C. for 3 h, and a sample taken for HPLC. In the HPLC chromatogram 2 peaks were observed in 95:5 to 90:10 ratio. The major compound so identified corresponded with the product. 2.49 Kg triethylamine were added and the mixture concentrated in vacuum to an oily residue. This residue was dissolved in 150 L ethyl acetate and the solution washed twice with 50 L water. The organic phase was concentrated in vacuum to an oily residue and degassed carefully to remove all volatiles. The oily residue was dissolved in 37 L toluene and the toluene solution slowly added to 300 L heptane. The product precipitated; the suspension was agitated for 3 min. The precipitate was collected and the cake washed with very little heptane. It was then dried in circulating air to constant weight. Yield: 12.63 kg of the title compound (28.78 mol; 78.3%).

EXAMPLE 18

Preparation of Methyl-2,3,4,6-tetra-O-acetyl-1-C-(2-chloro-4'-ethoxydiphenylmethan-3-yl)-α-D-glucopyranose

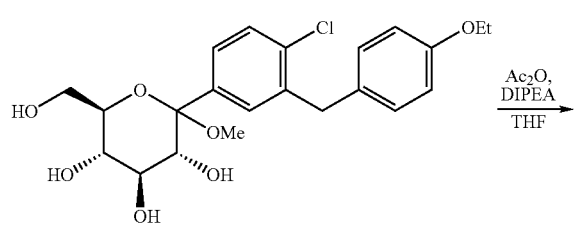

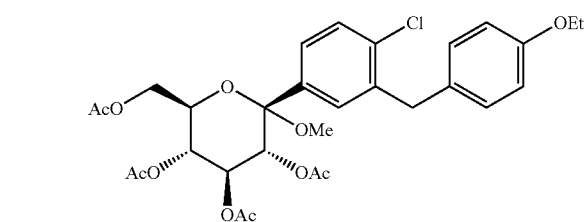

6.0 Kg methyl-1-C-(2-chloro-4'-ethoxydiphenylmethane-3-yl)-α-D-glucopyranoside were dissolved in 30 L THF and 13.04 kg DIPEA and 0.06 kg DMAP added. A sample was taken for HPLC. The mixture was cooled to 0–5° C. and 9.14 kg acetic anhydride added at such a rate that the temperature did not exceed +5° C. After complete addition the mixture was agitated at 0–5° C. for 1.5 h, then a sample taken for HPLC. The agitation was continued at 0–5° C. for another 1.5 h, then take a sample for HPLC. 30 L precooled (5° C.) MTBE were added and the mixture washed with 30 L ice-water then agitated for about 30 min at 5° C. The layers were separated and the aqueous layer extracted with 12 L MTBE. The combined organic phases were washed consecutively with 12 L 10% aqueous phosphoric acid, then twice with 12 L sat. Na-bicarbonate solution and with 8L brine. The solvent was evaporated at 40° C. in vacuum and the oily residue degassed carefully to obtain the title compound: Yield 7.52 kg (12.39 mol, 90.6%).

EXAMPLE 19

Preparation of 2,3,4,6-tetra-O-acetyl-1-C-(2-chloro-4'-ethoxydiphenylmethan-3-yl)-β-D-glucopyranose

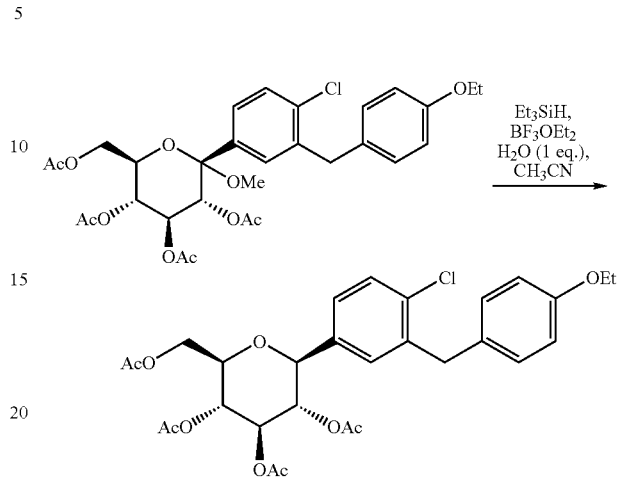

5.01 Kg of methyl-2,3,4,6-tetra-O-acetyl-1-C-(2-chloro-4'-ethoxydiphenylmethane-3-yl)-β-D-glucopyranoside (carefully degassed, no residual MTBE) were dissolved in 25 L acetonitrile. (Typically, the water content of the solution should be 0.02–0.07% by K. F; higher content may require correction for water.) The mixture was cooled to 10° C. and 0.15 L water added. 3.04 Kg triethylsilane were added, then a sample taken for HPLC. 2.34 Kg boron trifluoride etherate were added at such a rate that the internal temperature did not exceed 15° C. (After complete addition the temperature typically increases to about 25° C. Casual heating or cooling may be required, and the reaction time is normally from about 18–20 h.) Agitation was continued until at least 90% of starting material was converted. (Note: Additional TES and BF$_3$.Et$_2$O may be necessary.) The mixture was cooled to 15° C., and 25 L MTBE and 14.7 L sat. Na-bicarbonate solution added. The mixture was agitated for 20 min, the phases separated and the organic phase washed with another 14.7 L sat. Na-bicarbonate solution. The combined aqueous phases were extracted with 6 L MTBE, and the combined organic phases washed with 9 L brine. The organic phase was concentrated to a solid residue. The residue was then dissolved at 50–60° C. in 40 L ethanol. 0.5 Kg activated carbon was added and the mixture agitated at reflux for 10 min. The hot solution was polish filtered and the cake washed with 4.4 L hot ethanol. The solution was allowed to cool to room temp. within 3 h., then cooled to 0° C. and agitated for 1 h. The precipitate was collected and the cake washed with 8.8 L cold (0–5° C.) ethanol. The product was dried at 40° C. in vacuum to constant weight. Yield: 3.10 Kg of the title compound (5.36 mmol, 65.0%).

EXAMPLE 20

Preparation of 1-C-(2-chloro 4'-ethoxydiphenylmethan-3-yl)-β-D-glycopyranose

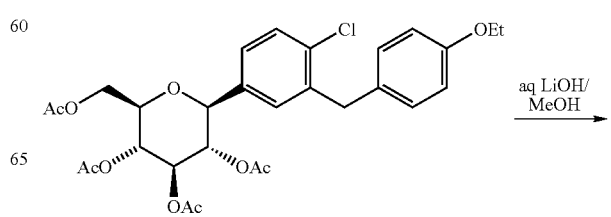

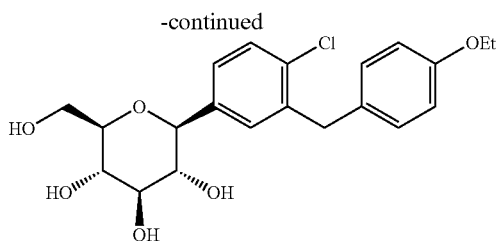

To a stirred solution of tetraacetylated β-C-glucoside (27.2 g, 49 mmol) prepared e.g. according to Example 19, in 480 mL of 2:3:1 THF/MeOH/H$_2$O was added LiOH monohydrate (2.3 g, 57 mmol) at 20° C. After stirring overnight, the volatiles were removed using a rotary evaporator. The residue, after being dissolved in EtOAc (300 mL), was washed 1× with brine (150 mL), 1× with brine (50 mL) containing 10 mL of 5% aq KHSO$_4$ and finally with brine (50 mL) prior to drying over Na$_2$SO$_4$. The volatiles were removed using a rotary evaporator and the resultant oil was reevaporated from a minimum amount of CH$_2$Cl$_2$ to yield 20.4 g of desired title C-arylglucoside as a glassy off white solid.

EXAMPLE 21

A. Telescoped Preparation of 2,3,4,6-tetra-O-acetyl-1-C-(4'-ethoxydiphenylmethan-3-yl)-β-D-glucopyranose

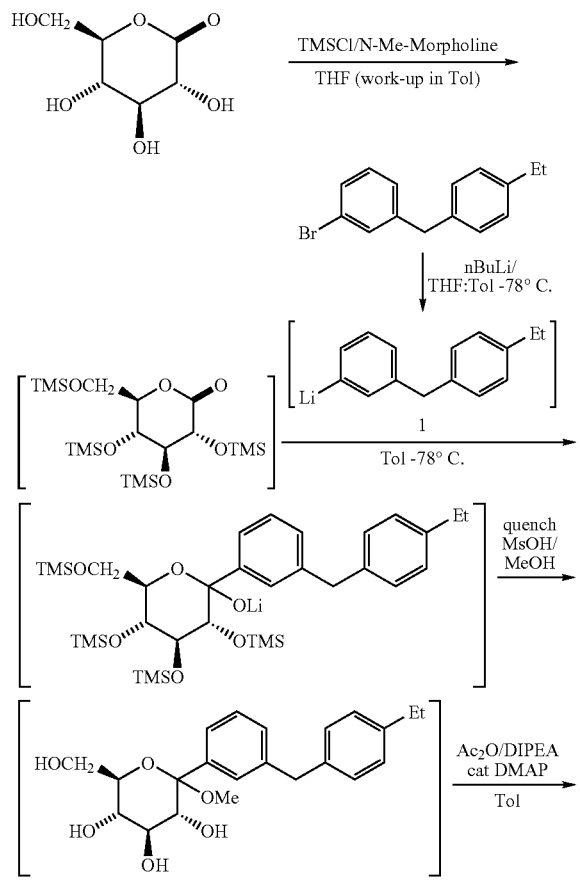

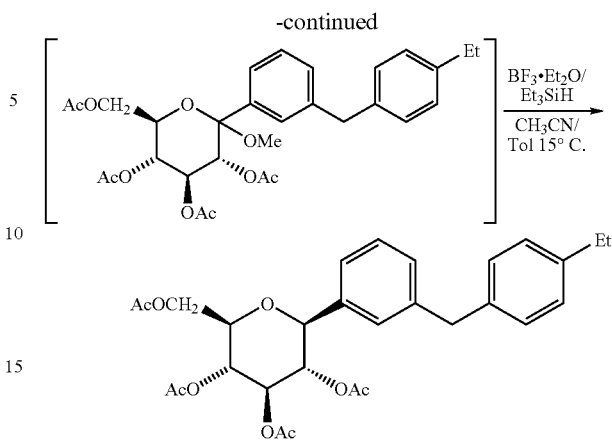

35 Kg of D-glucono-1,5-lactone were charged into a hastelloy reactor equipped with a thermocouple, mechanical agitator, and an addition funnel. Then 344.8 Kg THF (anhydrous) were added. Subsequently, 146.5 Kg 4-methylmorpholine (~8 eq.) were charged to the same reaction mixture and the slurry cooled to 5° C. 110.9 Kg Trimethylsilylchloride (6 eq.) were added and the slurry stirred for 15 min, after which the reaction mixture was warmed to 30–35° C. over 0.5 hr. After 5 hr, the reaction was complete (determined by GC). The reaction mixture was cooled to 0–5° C. and 454.1 kg of toluene were then added. The reaction was then quenched with 700 kg water. The reaction mixture was stirred for 10–15 minutes and the phases allowed to separate. The bottom aqueous layer was then removed. To the organic solution was charged a solution of 13.0 Kg NaH$_2$PO$_4$ in 260 Kg of water. The reaction mixture was agitated for 10 minutes and then the phases again separated. The bottom aqueous layer was removed and to it was added 273 kg water. The mixture was agitated for 10 minutes and the resulting aqueous phase again separated. The organic solution was distilled at 40–60° C. under reduced pressure (typical 23–25 in Hg), while adding toluene until the solution of silylated product in toluene has a KF of <0.05% water. The concentration of the silylated product was adjusted to ~0.1 g/mL by adding anhydrous toluene or distillation, as necessary. The yield of 2,3,4,6-tetra-O-trimethylsilyl-D-gluconolactone from the first step ranged from 91 to 98%, as measured by a GC assay based on the standard curve of the product (GC method) or by removing the solvent under reduced pressure to dryness.

To another reactor equipped with a thermocouple, mechanical agitator, and an addition funnel was charged 44.8 kg of 5-bromo-4'-ethyldiphenylmethane. 78.8 Kg of anhydrous THF was then added, followed by 281 kg of Toluene. The reactor was cooled to <–70° C. About 48.9 kg of n-BuLi were added (2.5 M in hexanes). The solution was stirred at <–70° C. under N$_2$ until the lithiation was determined to be complete by HPLC analysis. This lithiated anion solution derived from 5-bromo-4'-ethyldiphenylmethane was then added to the cooled 2,3,4,6-tetra-O-trimethylsilyl-D-gluconolactone solution prepared above at such a rate that the temperature remains <–70° C. The mixture was agitated at <–70° C. for at least 30 min, and an HPLC sample was taken to confirm reaction completion. 22.2 Kg solution of CH$_3$SO$_3$H (1.4 eq) in 334 kg MeOH were charged while maintaining the temperature <–60° C.

A sample was taken to confirm completion of the methyl glycosidation by taking 50 µL reaction mixture and quenching it with 10 mL CH$_3$CN for HPLC analysis. When the reaction was determined to be complete, it was quenched by addition of aq. sodium bicarbonate (11 Kg of NaHCO$_3$ in 220 kg water). The rich organic layer containing the product was washed with 220 kg water, the phases separated abd then the aqueous phases combined. The combined aqueous layer was extracted with 223 Kg ethyl actetate (this step is performed as needed). The product-rich organic layers were combined and the solvent distilled at 35–60° C. under reduced pressure (typically ~25 in Hg) until the KF of the solution was <0.07% H$_2$O and the amount of EtOAC was <1% relative to toluene as determined by GC analysis.

The yield of the product from the coupling performed using this process ranges from 72 to 89 M %; this concentration being determined by an HPLC assay based on a standard curve of the product.

To the solution of the methylglycoside was charged 0.11 kg DMAP, 64.33 kg diisopropylethyl amine, and 45.56 Kg of acetic anhydride. The solution was stirred at ≦35° C. until the reaction was determined to be complete by HPLC analysis. The reaction was judged to be complete when the area percent ratio (AP) of the intermediate acetylated species was ≦2% of the area of the tetra-acetylated product. Typical reaction times for this step run from 4–7 hours.

H$_3$PO$_4$ solution (48.44 Kg in 528 Kg water) was then charged to the reactor. The pH of the resultant lower aqueous layer was ≦3. (If the pH is not ≦3, additional H$_3$PO$_4$ may be added until the desired pH is reached.) The reaction was stirred for 10 min, then allowed to separate into phases. The bottom aqueous phase was separated and the organic phase washed with 245.54 kg water, after which the aqueous wash layer was separated. The organic solution was concentrated at atmospheric pressure to a volume of 4–6 L/kg of methyl-1-C-(4'-ethyldiphenylmethane-3-yl)-α-D-glucopyranoside (acetylated intermediate).

The reactor containing the acetylated intermediate was then charged with 174.8 kg acetonitrile and 1.6 kg water (1 mole equiv. with respect to acetylated intermediate). The mixture was then cooled to ≦15° C. and 30.3 kg of Et$_3$SiH added. Then 24.5 kg BF$_3$-Et$_2$O (2.1 equiv.) were charged over at least 20 minutes, while maintaining the temperature at <15° C. The reaction mixture was stirred until completion, as judged by HPLC analysis, about 4–7 h. The reaction mixture was then cooled to ≦20° C. The required amount of 2,2-dimethoxypropane was based on GC assay to determine the amount of Et$_3$SiH remaining and KF to determine the amount of H$_2$O remaining.

The reaction mixture was stirred until complete disappearance of Et$_3$SiH as determined by GC analysis, typically <2 h. An aqueous solution of NaHCO$_3$ (12.02 kg NaHCO$_3$ in 120.17 kg water) was added at ambient temperature until the pH of the aqueous phase was ≧6. The mixture was then agitated for at least 10 min, and the phases allowed to settle, at which point the lower aqueous phase was removed. 20% NaCl (24.03 kg NaCl in 120.17 kg water) was charged to the organic layer and the aqueous phase separated. The product rich organic phase was then distilled at atmospheric pressure until most of the acetonitrile was removed.

223.49 Kg toluene was charged and the distillation continued until the pot temperature reached at least 112° C. and a 4–6 L/kg concentration of methyl-1-C-(4'-ethyldiphenyl-methane-3-yl)-α-D-glucopyranoside was reached. While maintaining the temperature at >70° C., 240 Kg heptane were added. The solution was then cooled to approximately 60° C. over at least one hour and the slurry held at 60±10° C. for at least one hour.

Afterwards, the slurry was cooled to 20±10° C. temperature over at least one hour. It was then filtered in a Robatel Centrifuge and the cake washed with at least 2 cake volumes of heptane (57.7 Kg). The wet cake was dried under vacuum at ≦60° C., to an LOD of ≦0.2%, yielding ≧40 Kg of the title compound, (86%, Lab HPLC: 99 AP).

B. Preparation of 1-C-(4'-Ethyldiphenylmethane-3-yl)-β-D-glucopyranose L-Phenylalanine Complex

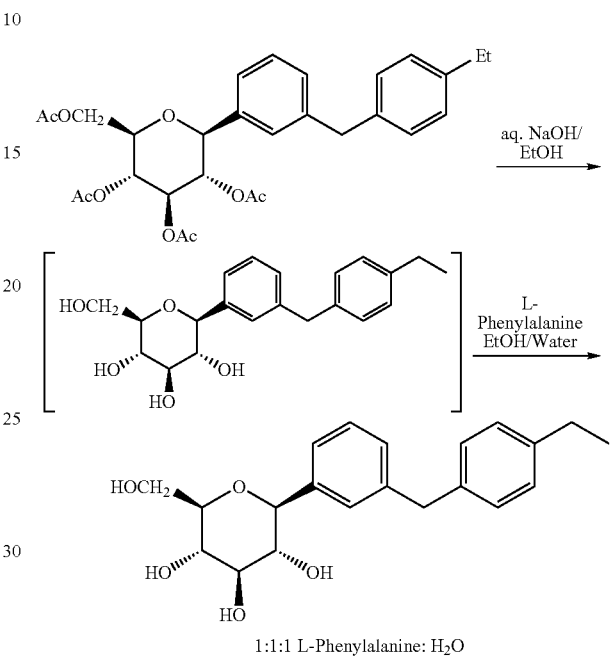

1:1:1 L-Phenylalanine: H$_2$O 68.70 Kg water were charged to a reactor equipped with a mechanical stirrer and nitrogen gas inlet. 64.40 Kg of 2,3,4,6-Tetra-O-acetyl-1-C-(4'-ethyldiphenyl-methane-3-yl)-β-D-glucopyranose were charged into the same reactor. 62.44 Kg EtOH (SDA-3A 190 proof) was added and the suspension stirred with minimum agitation at room temperature (20° C.) under a nitrogen atmosphere.

0.1 N NaOH$_{(aq)}$(57.02 kg) was added at room temperature (medium agitation) and slowly heated to 40–50° C., after which the mixture was stirred for 1–2 h until the in-process HPLC AP of the deacetylated product in the solution was measured at >97% (excluding the solvent front and system peaks).

The solution was cooled to 20° C. and then 154.56 kg deionized water at room temperature added; the solution temperature was then adjusted to 18–25° C. The reaction was stirred for 1 hr (cloudy solution). Concentrated HCl (37%, ~123.44 Kg) was then added to adjust the pH to 6.3. 20.20 Kg of L-Phenylalanine was added, followed by a 141.68 kg water charge. The slurry was heated to 75° C. and the clear solution passed through a polish filter. 51.52 Kg hot (75° C.) deionized water was charged to rinse the filtering flask and the wash was then added to the reaction mixture to adjust the composition of the solvent to ~12 vol % EtOH in solution. The slurry was heated at 75° C. and then the clear solution cooled to ca. 57° C. 322 Gm seed crystals of the title compound were added. The slurry was cooled to 40° C. over 1 h and the pot temperature maintained at 40° C. for 4 h. The slurry was cooled to 18–25° C. over 2 h and stirred at this temperature for 12–16 hours, after which it was filtered through a Robatel Centrifuge filter. The filter cake was washed with cold (<10° C.) 322 kg water to remove byproducts NaCl and NaOAc. The water wash was continued until the conductivity of the wash was below 0.001 Ω⁻¹. The filter cake was washed with 290 kg EtOAc to remove excess product. The wet cake was dried under vacuum at 18–25° C. for at least 4 hours, then at 40° C. for at least 12 hours. The drying was stopped when the KF reading of an aliquot was 2.8–3.6% water. The 1-C-(4'-ethyldiphenylmethane-3-yl)-β-D-glucopyranose L-phenylalanine complex was isolated as a white solid (54–58 Kg, 80–88%).

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A method of preparing a compound of Formula (I) or a pharmaceutically acceptable complex thereof

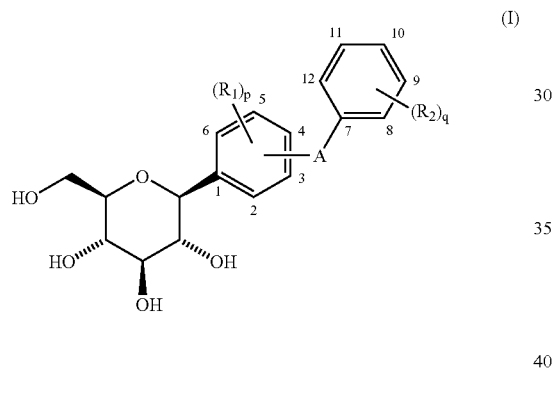

wherein:
R$_1$ is selected from the group consisting of hydrogen, a hydroxy group, bromine, chlorine, fluorine, an alkyl group, an alkoxy group, an alkylthio group, and an arylthio group, where p is 1 to 4, and with the proviso that bromine, chlorine and fluorine, when present, are only present in at least one of the 3-, 4- and 5-positions;
R$_2$ is selected from the group consisting of hydrogen, a hydroxy group, chlorine, fluorine, an alkyl group, an alkoxy group, and an alkylthio group, where q is 1 to 5; and
A is selected from the group consisting of a covalent bond, O, S, NH, and (CH$_2$)$_n$ where n is 1 to 3, and
with the proviso that when A is in the 4-position, R$_1$ is not bromine;
with the proviso that when one of R$_1$ is bromine; and
  if A is in the 3- or 6-position, then bromine is in the 5-position,
  if A is in the 2- or 5-position, then bromine is in the 3-position, and
  when bromine is in the 3-position, and A is in the 2- or 5-position, then R$_1$ groups in the 4- and 6-positions are the same and are not bromine, chlorine or fluorine, and when bromine is in the 5-position, and A is in the 3- or 6-position, then R$_1$ groups in the 2- and 4-positions are the same and are not bromine, chlorine or fluorine, said method comprising:

a) forming a compound of Formula (IV) from a lactone protected with an acid-labile protecting group

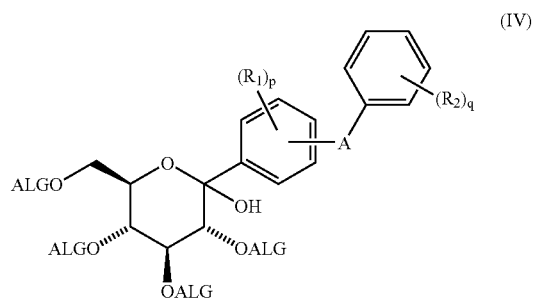

wherein ALG is an acid labile protecting group, b) glycosidating of the compound of Formula (IV) in the presence of a nucleophilic compound which has an R$_3$ group, with simultaneous removal of the acid-labile protecting group to form a compound of Formula (V);

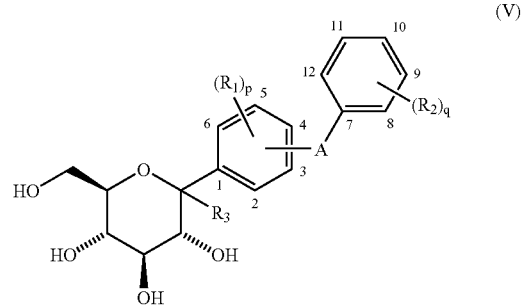

wherein R$_3$ is selected from the group consisting of an alkoxy group, an alkenyloxy group, an alkylthio group and an alkenylthio group;

c) reacting the compound of Formula (V) with an acylating agent to form a compound of Formula (VI);

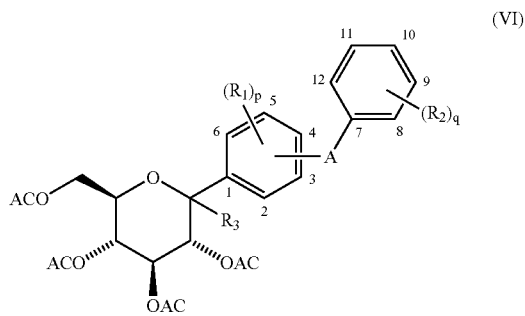

d) reducing the compound of Formula (VI) to provide a compound of Formula (VII); and

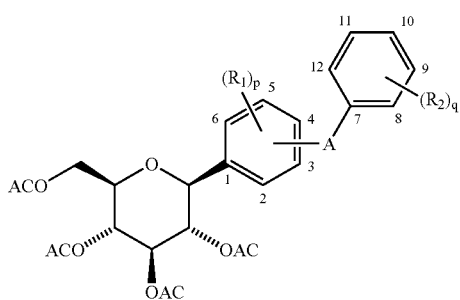

(VII)

e) removing acyl protecting group from the compound of Formula (VII) to provide a compound of Formula (I); wherein $R_1$, $R_2$, A, p and q are as defined hereinabove, and AC is an acyl protecting group.

2. The method of claim 1 wherein p is 1 to 2.
3. The method of claim 1 wherein q is 1 to 2.
4. The method of claim 1 wherein $R_1$ is selected from the group consisting of hydrogen, alkyl, chlorine, and fluorine.
5. The method of claim 4 wherein p is 1, and $R_1$ is selected from the group consisting of hydrogen, chlorine, and methyl.
6. The method of claim 5 wherein $R_1$ is at the 4-position.
7. The method of claim 1 wherein $R_2$ is selected from the group consisting of hydrogen, an alkyl group, an alkoxy group and an alkylthio group.
8. The method of claim 7 wherein q is 1, and $R_2$ is selected from the group consisting of ethyl, ethoxy and methylthio.
9. The method of claim 8 wherein $R_2$ is at the 4-position.
10. The method of claim 1 wherein A is ($CH_2$) located at the 3-position.
11. The method of claim 1 wherein the compound of Formula (I) is a compound of Formula (IA):

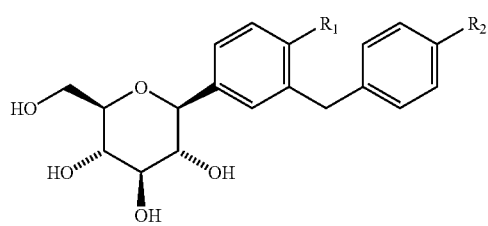

(IA)

wherein:
 $R_1$ is selected from hydrogen, an alkyl group, and chlorine; and
 $R_2$ is selected from hydrogen, an alkyl group, an alkoxy group, and an alkylthio group.

12. The method of claim 11 wherein $R_1$ is hydrogen and $R_2$ is ethyl.
13. The method of claim 11 wherein $R_1$ is chlorine and $R_2$ is ethoxy.
14. The method of claim 11 wherein $R_1$ is methyl and $R_2$ is methylthio.
15. The method of claim 1 further comprising reacting the compound of Formula (I) with at least one amino acid complex forming reagent to yield the pharmaceutically acceptable complex of the compound of Formula (I).
16. The method of claim 15 wherein the amino acid is L-phenylalanine.

17. The method as defined in claim 16 wherein the compound prepared is 1-C-(4'-ethyldiphenylmethane-3-yl)-β-D-glucopyranose-L-phenylalanine complex.
18. The method as defined in claim 15 wherein the compound prepared is a complex of a compound of Formula (I):

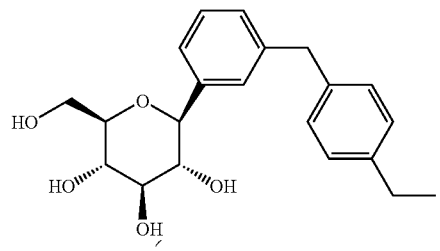

with an amino acid selected from L-phenylalanine or L-proline.

19. The method of claim 1 wherein steps (a) through (e) are performed in situ.
20. A method of preparing a compound of Formula (I) or a pharmaceutically acceptable complex thereof

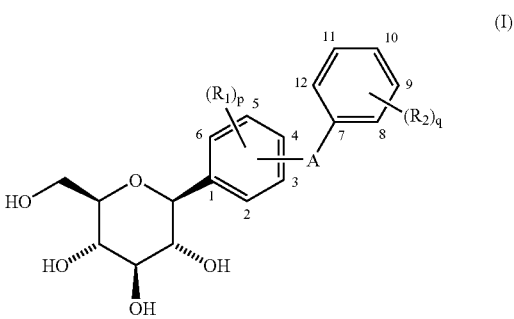

(I)

wherein:
 $R_1$ is 4-chloro;
 p is 1;
 q is 1;
 A is $(CH_2)_n$ where n is 1, and
 a) forming a compound of Formula (IV) from a lactone protected with an acid-labile protecting group

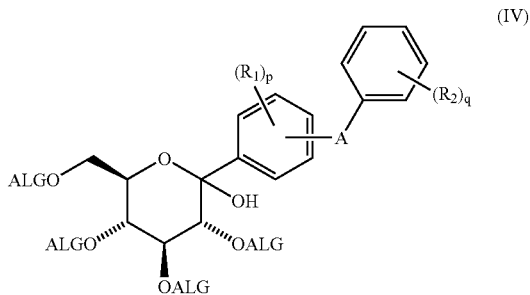

(IV)

wherein ALG is an acid labile protecting group,
 b) glycosidating the compound of Formula (IV) in the presence of a nucleophilic compound which has an $R_3$ group, which compound is methanol, with simultaneous removal of the acid-labile protecting group to form a compound of Formula (V);

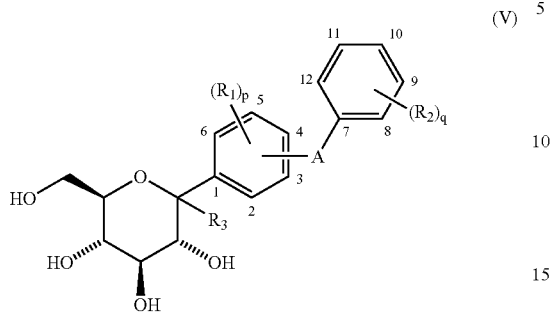

wherein $R_3$ is methoxy;

c) reacting the compound of Formula (V) with an acylating agent to form a compound of Formula (VI);

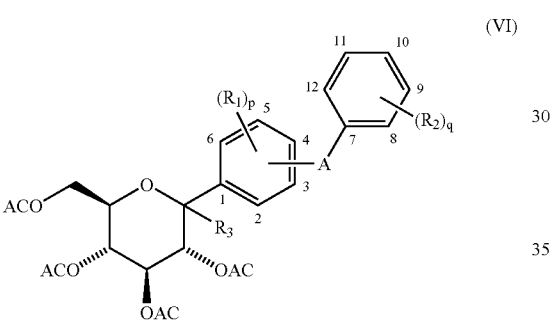

d) reducing the compound of Formula (VI) to provide a compound of Formula (VII); and

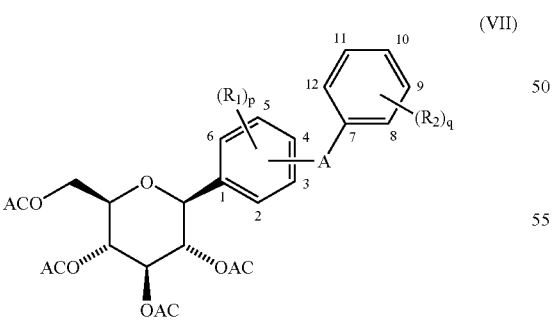

e) removing acyl protecting group from the compound of Formula (VII) to provide a compound of Formula (I);

wherein $R_1$, $R_2$, A, p and q are as defined hereinabove, and AC is an acyl protecting group.

21. A method of preparing a compound of Formula (I) or a pharmaceutically acceptable complex thereof

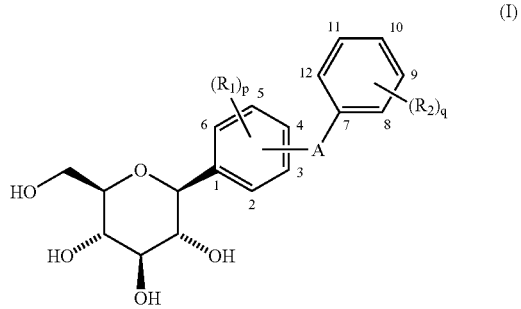

wherein
$R_1$ is 4-chloro;
p is 1;
$R_2$ is 10-ethyl;
q is 1;
A is $(CH_2)_n$ where n is 1, and
a0 forming a compound of Formula (IV) from a lactone protected with an acid-labile protecting group

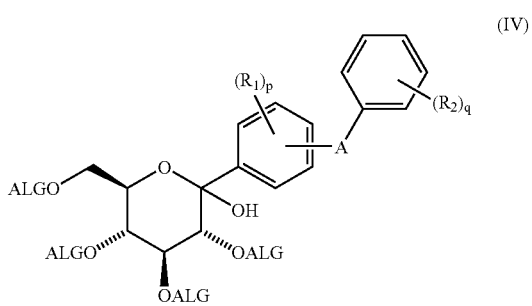

wherein ALG is an acid labile protecting group and A, $R_1$, p, $R_2$ and q are as defined above;

b) glycosidating the compound of Formula (IV) in the presence of a nucleophilic compound which has an $R_3$ group, which compound is methanol, with simultaneous removal of the acid-labile protecting group to form a compound of Formula (V);

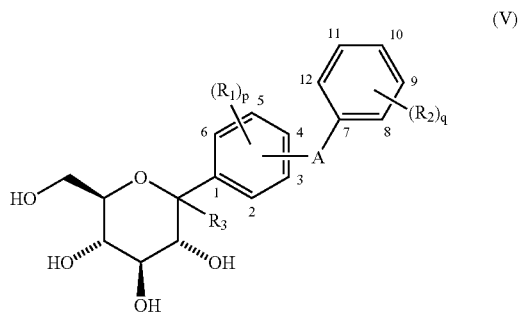

wherein $R_3$ is methoxy;

c) reacting the compound of Formula (V) with an acylating agent to form a compound of Formula (VI);

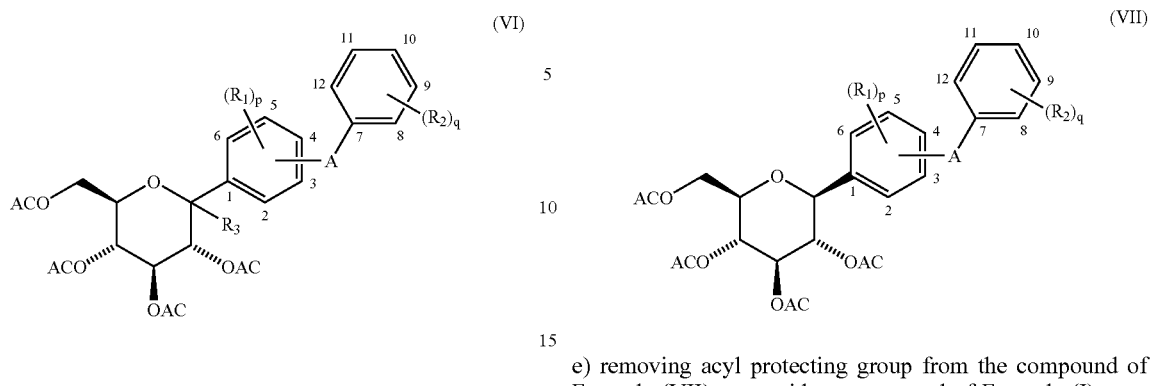
d) reducing the compound of Formula (VI) to provide a compound of Formula (VII); and
e) removing acyl protecting group from the compound of Formula (VII) to provide a compound of Formula (I);
wherein $R_1$, $R_2$, A, p and q are defined hereinabove, and AC is an acyl protecting group.
* * * * *

UNITED STATES PATENT AND TRADEMARK OFFICE
CERTIFICATE OF CORRECTION

PATENT NO. : 7,375,213 B2 Page 1 of 9
APPLICATION NO. : 10/745075
DATED : May 20, 2008
INVENTOR(S) : Prashant P. Deshpande et al.

It is certified that error appears in the above-identified patent and that said Letters Patent is hereby corrected as shown below:

At column 42, line 23, please delete the word "of" after glycosidating. Should read as follows:
-- b) glycosidating the compound of Formula (IV) in the --

At column 42, line 30, please delete the structure below as listed in the patent:

"
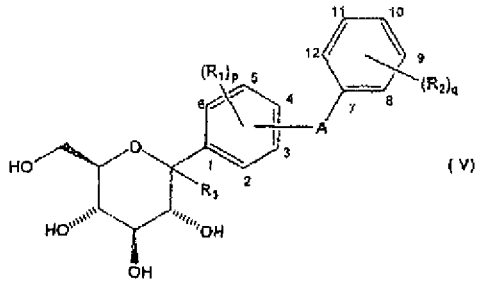
"

and replace it with the correct structure listed below:

--
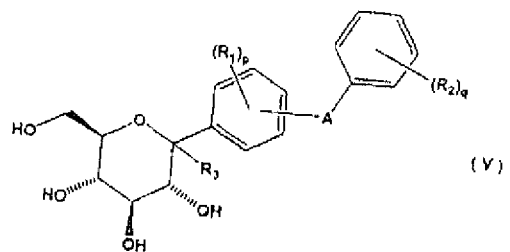
--

UNITED STATES PATENT AND TRADEMARK OFFICE
CERTIFICATE OF CORRECTION

| | | |
|---|---|---|
| PATENT NO. | : 7,375,213 B2 | Page 2 of 9 |
| APPLICATION NO. | : 10/745075 | |
| DATED | : May 20, 2008 | |
| INVENTOR(S) | : Prashant P. Deshpande et al. | |

It is certified that error appears in the above-identified patent and that said Letters Patent is hereby corrected as shown below:

At column 42, line 55, please delete the structure below as listed in the patent:

"

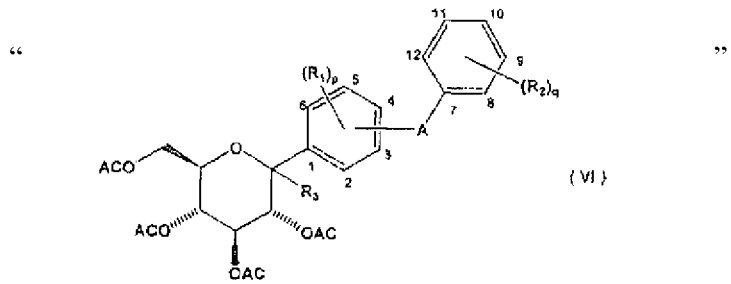

"

and replace it with the correct structure listed below:

--

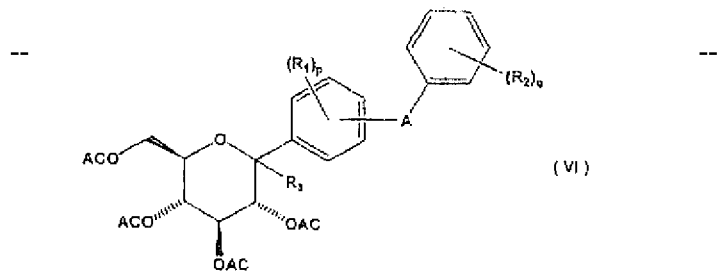

--

UNITED STATES PATENT AND TRADEMARK OFFICE
CERTIFICATE OF CORRECTION

PATENT NO.       : 7,375,213 B2
APPLICATION NO.  : 10/745075
DATED            : May 20, 2008
INVENTOR(S)      : Prashant P. Deshpande et al.

It is certified that error appears in the above-identified patent and that said Letters Patent is hereby corrected as shown below:

At column 43, line 1, please delete the structure below as listed in the patent:

"
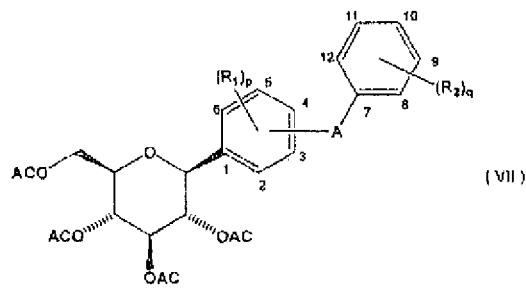
"

and replace it with the correct structure listed below:

--
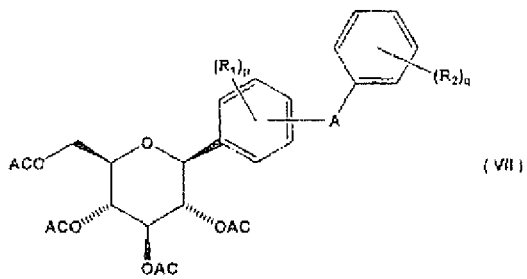
--

UNITED STATES PATENT AND TRADEMARK OFFICE
CERTIFICATE OF CORRECTION

PATENT NO. : 7,375,213 B2 Page 4 of 9
APPLICATION NO. : 10/745075
DATED : May 20, 2008
INVENTOR(S) : Prashant P. Deshpande et al.

It is certified that error appears in the above-identified patent and that said Letters Patent is hereby corrected as shown below:

At column 44, lines 44-45, in between "p is 1;" and "q is 1;" please insert --$R_2$ is 10-ethoxy--.

At column 45, line 5, please delete the structure below as listed in the patent:

"
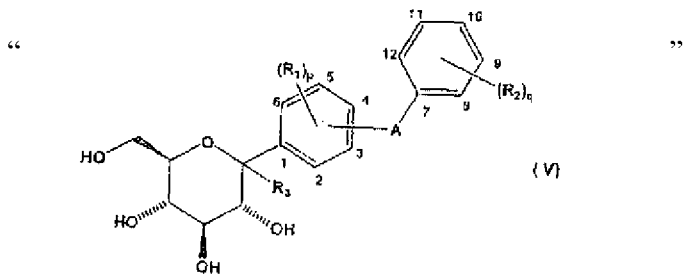
"

and replace it with the correct structure listed below:

--
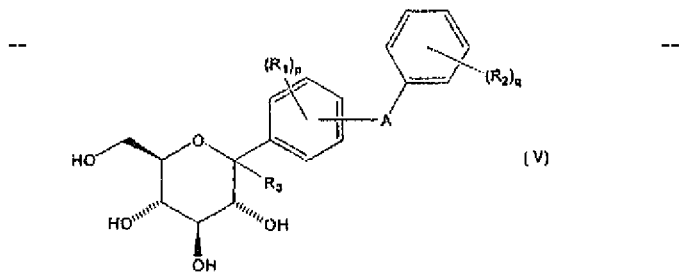
--

UNITED STATES PATENT AND TRADEMARK OFFICE
CERTIFICATE OF CORRECTION

| | | |
|---|---|---|
| PATENT NO. | : 7,375,213 B2 | Page 5 of 9 |
| APPLICATION NO. | : 10/745075 | |
| DATED | : May 20, 2008 | |
| INVENTOR(S) | : Prashant P. Deshpande et al. | |

It is certified that error appears in the above-identified patent and that said Letters Patent is hereby corrected as shown below:

At column 45, line 30, please delete the structure below as listed in the patent:

" 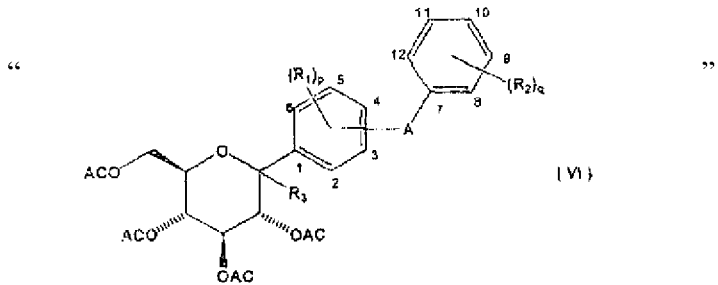 "

and replace it with the correct structure listed below:

-- 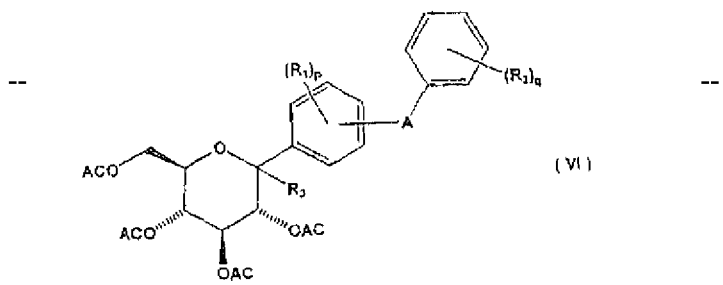 --

UNITED STATES PATENT AND TRADEMARK OFFICE
CERTIFICATE OF CORRECTION

PATENT NO. : 7,375,213 B2
APPLICATION NO. : 10/745075
DATED : May 20, 2008
INVENTOR(S) : Prashant P. Deshpande et al.

It is certified that error appears in the above-identified patent and that said Letters Patent is hereby corrected as shown below:

At column 45, line 50, please delete the structure below as listed in the patent:

" 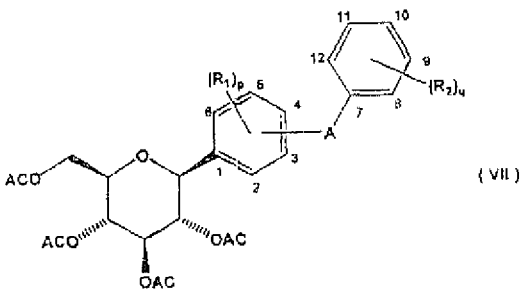 "

and replace it with the correct structure listed below:

-- 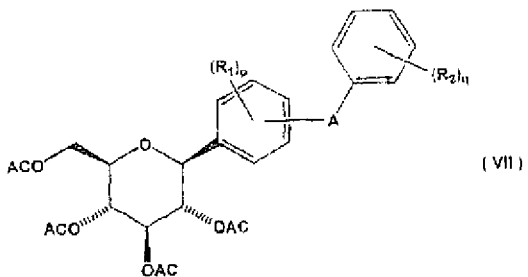 --

UNITED STATES PATENT AND TRADEMARK OFFICE
CERTIFICATE OF CORRECTION

PATENT NO. : 7,375,213 B2
APPLICATION NO. : 10/745075
DATED : May 20, 2008
INVENTOR(S) : Prashant P. Deshpande et al.

It is certified that error appears in the above-identified patent and that said Letters Patent is hereby corrected as shown below:

At column 46, line 23, please delete the "0" after the letter a and insert -- ) --.
Should read as follows:
-- a) forming a compound of Formula (IV) from lactone --

At column 46, line 55, please delete the structure below as listed in the patent:

"
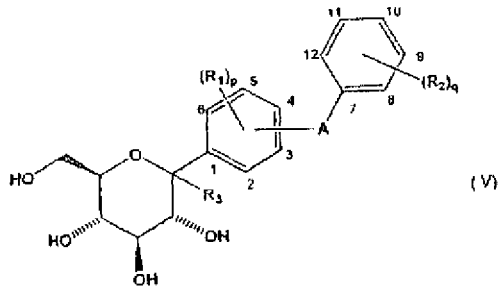
"

and replace it with the correct structure listed below:

--
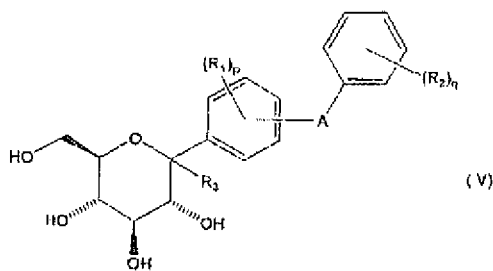
--

UNITED STATES PATENT AND TRADEMARK OFFICE
CERTIFICATE OF CORRECTION

| | | |
|---|---|---|
| PATENT NO. | : 7,375,213 B2 | Page 8 of 9 |
| APPLICATION NO. | : 10/745075 | |
| DATED | : May 20, 2008 | |
| INVENTOR(S) | : Prashant P. Deshpande et al. | |

It is certified that error appears in the above-identified patent and that said Letters Patent is hereby corrected as shown below:

At column 47, line 5, please delete the structure below as listed in the patent:

"
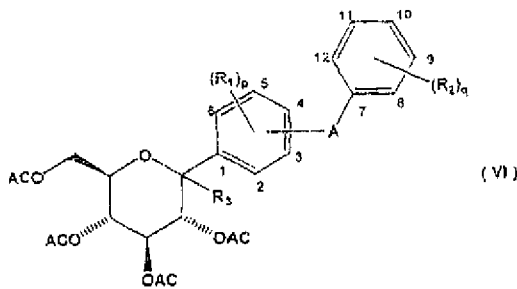
"

and replace it with the correct structure listed below:

--
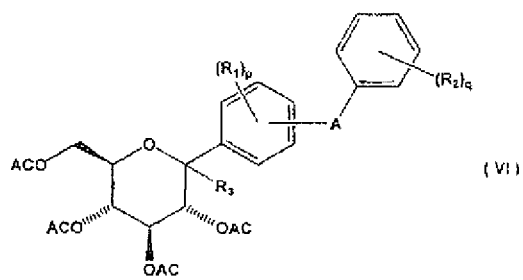
--

UNITED STATES PATENT AND TRADEMARK OFFICE
CERTIFICATE OF CORRECTION

PATENT NO. : 7,375,213 B2
APPLICATION NO. : 10/745075
DATED : May 20, 2008
INVENTOR(S) : Prashant P. Deshpande et al.

It is certified that error appears in the above-identified patent and that said Letters Patent is hereby corrected as shown below:

At column 48, line 5, please delete the structure below as listed in the patent:

" 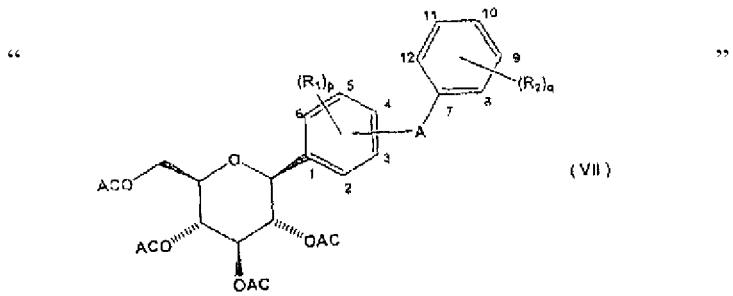 "

and replace it with the correct structure listed below:

-- 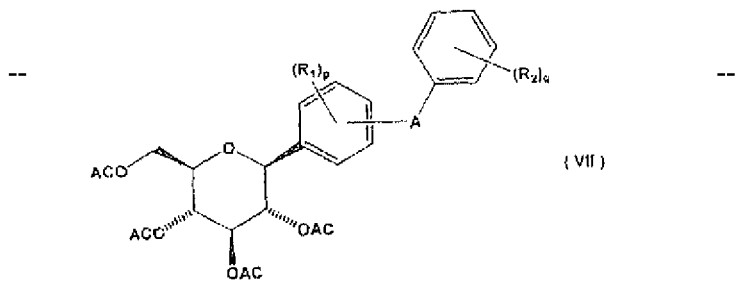 --

Signed and Sealed this

Twenty-first Day of April, 2009

JOHN DOLL
*Acting Director of the United States Patent and Trademark Office*